United States Patent [19]

Foster et al.

[11] Patent Number: 4,959,318
[45] Date of Patent: Sep. 25, 1990

[54] EXPRESSION OF PROTEIN C

[75] Inventors: Donald C. Foster; Mark J. Murray; Kathleen L. Berkner, Seattle, Wash.

[73] Assignee: ZymoGenetics, Inc., Seattle, Wash.

[21] Appl. No.: 924,462

[22] Filed: Oct. 29, 1986

Related U.S. Application Data

[63] Continuation-in-part of Ser. No. 749,600, Jun. 27, 1985.

[51] Int. Cl.[5] .................... C12N 15/00; C12N 9/64; C12N 5/02; C07H 15/12
[52] U.S. Cl. .................... 435/69.1; 435/226; 435/240.25; 435/320; 435/849; 536/27; 935/14; 935/29; 935/32; 935/48
[58] Field of Search .................... 435/68, 70, 91, 172.3, 435/235, 243, 317, 226, 247, 320, 317.1; 536/27; 935/11, 23, 32, 34, 57, 60, 70

[56] References Cited

U.S. PATENT DOCUMENTS

| | | | |
|---|---|---|---|
| 4,604,285 | 8/1986 | Smith et al. | 424/94 |
| 4,770,999 | 11/1988 | Kaufman et al. | 435/68 |
| 4,775,624 | 10/1988 | Bang et al. | 435/226 |
| 4,784,950 | 11/1988 | Hagen et al. | 435/68 |

FOREIGN PATENT DOCUMENTS 138222 4/1985 European Pat. Off.
WO85/00521 2/1985 United Kingdom.

OTHER PUBLICATIONS

Foster and Davie (1984) *Proceedings National Academy Sciences, U.S.A.*, vol. 81, pp. 4766–4770.
Degen et al. (1983) *Biochemistry*, vol. 22, pp. 2087–2097.
Ferlund et al. (1982) *Journal Biological Chemistry*, vol. 257, pp. 12170–12179.
Stenflo et al. (1982) *Journal of Biological Chemistry*, vol. 257, pp. 12180–12190.
Kaufman and Sharp (1982) *Molecular and Cellular Biology*, vol. 2, pp. 1304–1319.
Kaufman (1985) *Proceedings National Academy Sciences U.S.A.*, vol. 82, pp. 689–693.
Hermonat et al. (1984) *Proceedings National Academy Sciences U.S.A.*, vol. 81, pp. 6466–6470.
Esmon et al. (1981) *Proceedings National Academy Sciences U.S.A.*, vol. 78, pp. 2249–2252.
Plutzky et al. (1986) *Proceedings National Academy Sciences, U.S.A.*, vol. 83, pp. 546–550.
Ginsburg et al. (1985) *Science*, vol. 228, pp. 1401–1406.
Kisiel et al., *Biochem.* 16:5824–5831, 1977.
Long et al., *PNAS* 81:5653–5656, 1984.
Walker et al., *Biochim et Biophys. Acta 571*: 333–342, 1979.
Beckmann et al., *Fed. Proc.* 44:3951, 1985.
Katayama et al., *PNAS* 76:4990–4994, 1979.
McMullen et al., *Biochem. and Biophys. Res. Comm.* 115:8–14, 1983.
Miletech and Broze, "Characterization of Monoclonal Antibody Specific for the Heavy Chain of Non-Activated Human Protein C," Nov. 1983.
Kisiel and Davie, *Methods in Enzymology* 80:320–332, 1981.
Griffin et al., *J. Clin. Invest.* 68:1370–1373, 1981.
Van Hinsbergh et al., *Blood* 65:444–451, 1985.
Kisiel et al., *Behring Inst. Mitt.* 73:29–43, 1983.
Gardiner et al., *Prog. Hematol* 13:265–278, 1983.

(List continued on next page.)

*Primary Examiner*—Thomas D. Mays
*Attorney, Agent, or Firm*—Seed and Berry

[57] ABSTRACT

Genomic and cDNA sequences coding for a protein having substantially the same biological activity as human protein C and recombinant transfer vectors comprising these sequences are disclosed.

Methods are disclosed for producing a protein which has substantially the same biological activity as human protein C. The protein, which may be in the form of activated protein C, is produced by mammalian host cells transfected with a plasmid capable of integration in mammalian host cell DNA. The plasmid includes a promoter followed downstream by a nucleotide sequence which encodes a protein having substantially the same structure and/or activity as human protein C, the nucleotide sequence being followed downstream by a polyadenylation signal.

20 Claims, 15 Drawing Sheets

OTHER PUBLICATIONS

Comp et al., *J. Clin. Invest.* 68:1221–1228, 1981.
Sakata et al., *PNAS 82*:1121–1125, 1985.
Broekmans et al., *New Eng. Journ. Med.* 309:340–344, 1983.
Seligsohn et al., *New Eng. Journ. Med. 310*:559–562, 1984.
Marlar et al., *Blood 59*:1067–1072, 1982.
Foster et al., *PNAS 82*:4673–4677, 1985.
Beckman et al., *Nucleic Acids Research 13*:5233–5247, 1985.
Kisiel, *J. Clin. Invest. 64*:761–769, 1979.

FIG. 2

```
                                                                    G CCT CTC ATC CCC CCA GGA     19

-42           -40                                    -30
                           Met Trp Gln Leu Thr Ser Leu Leu Phe Val Ala Thr
CGC CGA ACT TCC AGT ATC TCC ACG ACC CCC TGT CCC ACT CCC TCC AGA ATG TCC CAG CTC ACA AGC CTC TTC GTG GCC ACC     109

-20                                          -10                        -1 +1
Trp Gly Ile Ser Gly Thr Pro Ala Pro Leu Asp Ser Val Phe Ser Ser Ser Glu Arg Ala His Gln Val Leu Arg Ile Arg Lys Arg Ala
TGG GGA ATT TCC GGC ACC CCA GCT CCT CTT GAC TCA GTC TTC TCC AGC AGC TCC GAG AGG GCC CAC CAG GTG CTG CGG ATC CGG AAA CGT GCC     199

10                                         20                          30
Asn Ser Phe Leu Glu Glu Leu Arg His Ser Ser Leu Glu Arg Glu Cys Ile Glu Cys Asp Phe Glu Glu Ala Lys Glu Ile Phe
AAC TCC TTC CTG GAG GAG CTC CGT CAC AGC AGC CTG GAG CGG GAG TGC ATA GAG GAG ATC TGT GAC TTC GAG GAG GCC AAG GAA ATT TTC     289

40                                      50                                 60
Gln Asn Val Asp Asp Thr Leu Ala Phe Trp Ser Lys His Val Asp Gly Asp Gln Cys Leu Val Leu Pro Leu Glu His Pro Cys Ala Ser
CAA AAT GTG GAT GAT ACA CTG GCC TTC TGG TCC AAG CAC GTC GAC GGT GAC CAG TGC TTG GTC TTG CCC TTG GAG CAC CCG TGC GCC AGC     379

70                                    80                              90
Leu Cys Cys Gly His Gly Thr Cys Ile Asp Gly Ile Gly Ser Phe Ser Cys Asp Cys Arg Ser Gly Trp Glu Gly Arg Phe Cys Gln Arg
CTC TGC TGC GGG CAC GGC ACC TGC ATC GAC GGC ATC GGC AGC TTC AGC TGC GAC TGC CGC AGC GGC TGG GAG GGG CGC TTC TGC CAG CGC     469

100                                     110                                   120
Glu Val Ser Phe Leu Asn Cys Ser Leu Asp Asn Gly Gly Cys Thr His Tyr Cys Leu Glu Glu Val Gly Trp Arg Arg Cys Ser Cys Ala
GAG GTG AGC TTC CTC AAT TGC TCT CTG GAC AAC GGC GGC TGC ACC CAT TAC TGC CTA GAG GAG GTG GGC TGG CGG CGC TGT AGC TGT GCC     559

130                                       140                                   150
Pro Gly Tyr Lys Leu Gly Asp Asp Leu Leu Gln Cys His Pro Ala Val Lys Phe Pro Cys Gly Arg Pro Trp Lys Arg Met Glu Lys Lys
CCT GGC TAC AAG CTC GGG GAC GAC CTC CTG CAG TGT CAC CCC GCA GTC AAG TTC CCT TGT GGG AGG CCC TGG AAG CGG ATG GAG AAG AAG     649

160                                    170                         180
Arg Ser His Leu Lys Arg Asp Thr Glu Asp Gln Glu Asp Gln Val Asp Pro Arg Leu Ile Asp Gly Lys Met Thr Arg Arg Gly Asp Ser
CGC AGT CAT CTC AAA CGA ACA GAA GAC CAA GAA GAC CAA GTA GAT CCG CGG CTC ATT GAT GGG AAG ATG ACC AGG CGG GGA GAC ACC     739
```

```
                                    190                                    200                                    210
Pro Trp Gln Val Val Leu Leu Asp Ser Lys Lys Leu Ala Cys Gly Ala Val Leu Ile His Pro Ser Trp Val Leu Thr Ala Ala His
CCC TGG CAG GTG GTG CTC CTC GAC TCA AAG AAG CTG GCC TGC GGG GCA CTC ATC CCC TCC TGG GTG CTC ACA CCG GCC CAC      829

220                                    230                                    240
Cys Met Asp Glu Ser Lys Leu Leu Val Arg Leu Gly Glu Tyr Asp Leu Arg Arg Trp Glu Lys Trp Glu Leu Asp Leu Asp Ile Lys
TGC ATG GAC GAG TCC AAG CTC CTT GTC AGG CTT GGA GAG TAT GAC CTC CGG CGC TGG GAG AAG TGG GAG CTG GAC CTG GAC ATC AAG      919

250                                    260                                    270
Glu Val Phe Val His Pro Asn Tyr Ser Lys Ser Thr Thr Asp Asn Asp Ile Ala Leu Leu His Leu Ala Gln Pro Ala Thr Leu Ser Gln
GAG GTC TTC GTC CAC CCC AAC TAC AGC AAG AGC ACC ACC GAC AAT GAC ATC GCA CTG CTG CAC CTC GCC CAG CCC GCC ACC CTC TCG CAG      1009

280                                    290                                    300
Thr Ile Val Pro Ile Cys Leu Pro Asp Ser Gly Leu Ala Glu Arg Glu Leu Asn Gln Ala Gly Gln Glu Thr Leu Val Thr Gly Trp Gly
ACC ATA GTC CCC ATC TGC CTC CCC GAC AGC GGC CTT GCA GAG CGC GAG CTC AAT CAG GCC GGC CAG GAG ACC CTC GTG ACG GGT CTG GGC      1099

310                                    320                                    330
Tyr His Ser Ser Arg Glu Lys Glu Ala Lys Arg Asn Arg Thr Phe Val Leu Asn Phe Ile Lys Ile Pro Val Val Pro His Asn Glu Cys
TAC CAC AGC AGC CGA GAG AAG GAG GCC AAG AGA AAC CGC ACC TTC GTC CTC AAC TTC ATC AAG ATT CCC GTC GTC CCG CAC AAT GAG TGC      1189

340                                    350                                    360
Ser Glu Val Met Ser Asn Met Val Ser Glu Asn Met Leu Cys Ala Gly Ile Leu Gly Asp Arg Gln Asp Ala Cys Glu Gly Asp Ser Gly
AGC GAG GTC ATG AGC AAC ATG GTG TCT GAG AAC ATG CTG TGT GCC GGC ATC CTC GGG GAC CGG CAG GAT GCC TGC GAG GGC GAC AGT GGG      1279

370                                    380                                    390
Gly Pro Met Val Ala Ser Phe His Gly Thr Trp Phe Leu Val Gly Leu Val Ser Trp Gly Glu Gly Cys Gly Leu Leu His Asn Tyr Gly
GGG CCC ATG GTC GCC TCC TTC CAC GGC ACC TGG TTC CTG GTG GGC CTG GTG AGC TGG GGT GAG GGC TGT GGG CTC CTT CAC AAC TAC GGC      1369

400                                    410                                    419
Val Tyr Thr Lys Val Ser Arg Tyr Leu Asp Trp Ile His Gly His Ile Arg Asp Lys Glu Ala Pro Gln Lys Ser Trp Ala Pro STOP
GTT TAC ACC AAA GTC AGC CGC TAC CTC GAC TGG ATC CAT GGG CAC ATC AGA GAC AAG GAA GCC CCT CAG AAG AGC TGG GCA CCT TAG CGA      1459
```

FIG. 2 CONT.

```
CCC TCC CTG CAG GGC TGG GCT TTT GCA TGG CAA TGG ATG GGA CAT TAA AGG CAC ATG TAA CAA GCA CAC CGG CCT GCT GTT CTG TCC TTC      1549

CAT CCC TCT TTT GGG CTC TTC TCG AGG GAA GTA ACA TTT ACT GAG CAC CTG TTG TAT GTC ACA TGC CTT ATG AAT AGA ATC TTA ACT CCT      1639

AGA GCA ACT CTG TCG GGT GGG GAG GAG CAG ATC CAA GTT TTC CGG GGT CTA AAG CTG TGT GTG TTG AGG CGC ATA CTC TGT TTA TGA AAA      1729

ACA ATA AAA AAC ACA ACC ACG AAA AAA AAA ₃'      1759
```

EXPRESSION OF PROTEIN C

CROSS-REFERENCE TO RELATED APPLICATION

This application is a continuation-in-part of U.S. application Ser. No. 749,600, filed June 27, 1985, which application is pending.

TECHNICAL FIELD

The present invention relates generally to plasma proteins and DNA sequences encoding them, and more specifically, to the expression of proteins having substantially the same structure and/or activity as human protein C, or human activated protein C.

BACKGROUND ART

Protein C is a zymogen, or precursor, of a serine protease which plays an important role in the regulation of blood coagulation and generation of fibrinolytic activity in vivo. It is synthesized in the liver as a single-chain polypeptide which undergoes considerable processing to give rise to a two-chain molecule comprising heavy (Mr=40,000) and light (Mr=21,000) chains held together by a disulfide bond. The circulating two-chain intermediate is converted to the biologically active form of the molecule, known as "activated protein C" (APC), by the thrombinmediated cleavage of a 12-residue peptide from the aminoterminus of the heavy chain. The cleavage reaction is augmented in vivo by thrombomodulin, an endothelial cell cofactor (Esmon and Owen, *Proc. Natl. Acad. Sci. USA* 78: 2249–2252, 1981).

Protein C is a vitamin K-dependent glycoprotein which contains approximately nine residues of gammacarboxyglutamic acid (Gla) and one equivalent of betahydroxyaspartic acid which are formed by post-translational modifications of glutamic acid and aspartic acid residues, respectively. The post-translational formation of specific gamma-carboxyglutamic acid residues in protein C requires vitamin K. These unusual amino acid residues bind to calcium ions and are believed to be responsible for the interaction of the protein with phospholipid, which is required for the biological activity of protein C.

In contrast to the coagulation-promoting action of other vitamin K-dependent plasma proteins, such as factor VII, factor IX, and factor X, activated protein C acts as a regulator of the coagulation process through the inactivation of factor Va and factor VIIIa by limited proteolysis. The inactivation of factors Va and VIIIa by protein C is dependent upon the presence of acidic phospholipids and calcium ions. Protein S has been reported to regulate this activity by accelerating the APC-catalyzed proteolysis of factor Va (Walker, *J. Biol. Chem.* 255: 5521–5524, 1980).

Protein C has also been implicated in the action of tissue-type plasminogen activator (Kisiel and Fujikawa, *Behring Inst. Mitt.* 73: 29–42, 1983). Infusion of bovine APC into dogs results in increased plasminogen activator activity (Comp and Esmon, *J. Clin. Invest.* 68: 1221–1228, 1981). Recent studies (Sakata et al., *Proc. Natl. Acad. Sci. USA* 82: 1121–1125, 1985) have shown that addition of APC to cultured endothelial cells leads to a rapid, dosedependent increase in fibrinolytic activity in the conditioned media, reflecting increases in the activity of both urokinase-related and tissue-type plasminogen activators by the cells. APC treatment also results in a dose-dependent decrease in antiactivator activity.

Protein C deficiency is associated with recurrent thrombotic disease (Broekmans et al., *New Eng. J. Med.* 309: 340–344, 1983; and Seligsohn et al., *New Eng. J. Med.* 310: 559–562, 1984) and may result from genetic disorder or from trauma, such as liver disease or surgery. This condition is generally treated with oral anticoagulants. Beneficial effects have also been obtained through the infusion of protein C-containing normal plasma (see Gardiner and Griffin in *Prog. in Hematology*, ed. Brown, Grune & Stratton, N.Y., 13: 265–278). In addition, some investigators have discovered that the anti-coagulant activity of protein C is useful in treating thrombotic disorders, such as venous thrombosis (Smith et al., PCT Publication No. WO 85/00521). In some parts of the world, it is estimated that approximately 1 in 16,000 individuals exhibit protein C deficiency. Further, a total deficiency in protein C is fatal in newborns.

While natural protein C may be purified from clotting factor concentrates (Marlar et al., *Blood* 59: 1067–1072) or from plasma (Kisiel, ibid), it is a complex and expensive process, in part due to the limited availability of the starting material and the low concentration of protein C in plasma. Furthermore, the therapeutic use of products derived from human blood carries the risk of disease transmission by, for example, hepatitis virus, cytomegalovirus, or the causative agent of acquired immune deficiency syndrome (AIDS). In view of protein C's clinical applicability in the treatment of thrombotic disorders, the production of useful quantities of protein C and activated protein C is clearly invaluable.

DISCLOSURE OF THE INVENTION

Briefly stated, the present invention discloses a DNA sequence which, within a continuous open reading frame, codes for a protein having substantially the same structure and/or biological activity as human protein C or human activated protein C. A related aspect of the present invention is directed toward a DNA sequence which codes for a protein having subtantially the same biological activity as human protein C or human activated protein C, the sequence further encoding the pre-pro peptide of Factor VII. Yet another DNA sequence which codes for a protein having subtantially the same biological activity as human protein C or human activated protein C is disclosed, the sequence further encoding the amino acid sequence Arg-Arg-Lys-Arg at the cleavage site between the light and heavy chains.

In addition, the present invention discloses an expression vector capable of integration in mammalian host cell DNA, including a promoter followed downstream by a nucleotide sequence which encodes a protein having substantially the same structure and/or activity as human protein C or human activated protein C, transcription of the nucleotide sequence being directed by the promoter. The nucleotide sequence is followed downstream by a polyadenylation signal. In one embodiment, the expression vector includes a selectable marker located between the nucleotide sequence and the polyadenylation signal, transcription of the selectable marker being directed by the promoter. The expression vector may also include a set of RNA splice sites.

A related aspect of the present invention discloses mammalian cells transfected to express a protein which, upon activation, has substantially the same biological activity as human activated protein C. The mammalian cells are transfected with an expression vector capable of integration in mammalian host cell DNA, the expression vector including a promoter followed downstream by a nucleotide sequence which encodes a protein having substantially the same structure and/or activity as human protein C. Within one embodiment, a selectable marker is also introduced into the cells and stably transfected cells are selected. Mammalian cells transfected to express a protein which has substantially the same biological activity as human activated protein C are also disclosed.

A further aspect of the invention discloses a method for producing a protein which, upon activation, has substantially the same biological activity as human activated protein C. The method comprises (a) introducing into a mammalian host cell an expression unit comprising a sequence which encodes a protein having substantially the same structure and/or activity as human protein C; (b) growing said mammalian host cell in an appropriate medium; and (c) isolating the protein product encoded by said expression unit and produced by said mammalian host cell. The protein product produced according to this method is also disclosed. A method for producing a protein which has substantially the same structure and/or biological activity as human activated protein C is also disclosed.

The proteins described within the present invention may be used as active therapeutic substances, including use in the regulation of blood coagulation. Further, these proteins may be combined with a physiologically acceptable carrier and/or diluent to provide suitable pharmaceutical compositions.

Other aspects of the invention will become evident upon reference to the detailed description and attached drawings.

BRIEF DESCRIPTION OF THE DRAWINGS

FIG. 2 illustrates the nucleotide sequence of the complete protein C cDNA and the deduced amino acid sequence of protein C. Arrows indicate cleavage sites for removal of the connecting dipeptide and activation peptide.

FIG. 4 illustrates the complete genomic sequence, including exons and introns of the human protein C gene. Arrowheads indicate intron-exon splice junctions. The polyadenylation or processing sequences of A-T-T-A-A-A and A-A-T-A-A-A at the 3' end are boxed. ◇, potential carbohydrate attachment sites; ◀, apparent cleavage sites for processing of the connecting dipeptide; ↓, site of cleavage in the heavy chain when protein C is converted to activated protein C; •, sites of polyadenylation.

BEST MODE FOR CARRYING OUT THE INVENTION

Figure 1:
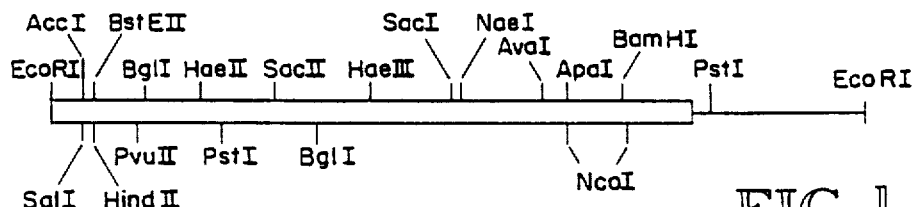
FIG. 1 is partial restriction map of the protein C cDNA in pHCλ6L. The coding region is indicated by an open box.

Prior to setting forth the invention, it may be helpful to an understanding thereof to set forth definitions of certain terms to be used hereinafter.

Biological Activity: A function or set of functions performed by a molecule in a biological context (i.e., in an organism or an in vitro facsimile). Biological activities of proteins may be divided into catalytic and effector activities. Catalytic activities of the vitamin K-dependent plasma proteins generally involve the specific proteolytic cleavage of other plasma proteins, resulting in activation or deactivation of the substrate. Effector activities include specific binding of the biologically active molecule to calcium or other small molecules, to macromolecules, such as proteins, or to cells. Effector activity frequently augments, or is essential to, catalytic activity under physiological conditions.

For protein C, biological activity is characterized by its anticoagulant and fibrinolytic properties. Protein C, when activated, inactivates factor Va and factor VIIIa in the presence of phospholipid and calcium. Protein S appears to be involved in the regulation of this function (Walker, ibid). Activated protein C also enhances fibrinolysis, an effect believed to be mediated by the lowering of levels of plasminogen activator inhibitors (van Hinsbergh et al., *Blood* 65: 444–451, 1985). As more fully described below, that portion of protein C encoded by exons VII and VIII of the protein C gene is primarily responsible for its catalytic activities.

Pre-pro peptide: An amino acid sequence which occurs at the amino terminus of some proteins and is generally cleaved from the protein during translocation. Pre-pro peptides comprise sequences directing the protein into the secretion pathway of the cell (signal sequences) and are characterized by the presence of a core of hydrophobic amino acids. They may also comprise processing signals. As used herein, the term "pre-pro peptide" may also mean a portion of the naturally occuring pre-pro peptide.

Expression Unit: A DNA construct comprising a primary nucleotide sequence encoding a protein of interest, together with other nucleotide sequences which direct and control the transcription of the primary nucleotide sequence. An expression unit consists of at least the primary nucleotide sequence and a promoter sequence located upstream from and operably linked to the primary nucleotide sequence and a polyadenylation signal located downstream. Additional genetic elements may also be included to enhance efficiency of expression. These elements include enhancer sequences, leaders, and mRNA splice sites.

Expression Vector: A DNA molecule which contains, inter alia, a DNA sequence encoding a protein of interest together with a promoter and other sequences which facilitate expression of the protein. Expression vectors further contain genetic information which provides for their replication in a host cell. Examples of expression vectors commonly used for recombinant DNA are plasmids and certain viruses, although they may contain elements of both. They also may include a selectable marker.

As noted above, protein C is produced in the liver and requires vitamin K for its biosynthesis. Vitamin K is necessary for the formation of specific gamma-carboxyglutamic acid residues in the amino-terminal region of the light chain. These amino acid residues are formed by a post-translational modification, and are required for calcium-mediated binding to phospholipid. In addition, protein C contains one beta-hydroxyaspartic acid residue which is also formed in a post-translational modification. However, the role of this amino acid residue is not known.

Given the fact that the activity of protein C is dependent upon post-translational modifications involving the gamma carboxylation of specific glutamic acid residues and cleavage to the two-chain form, and may also be dependent upon the hydroxylation of a specific aspartic acid residue, it is unlikely that an active product could be produced through the cloning and expression of protein C in a microorganism.

Accordingly, the present invention provides a method of producing a protein which is gamma-carboxylated and, upon activation, has the biological activity of human activated protein C through the use of mammalian cells transfected to permanently express the protein.

The present invention further provides a method for producing a protein which is gamma-carboxylated and has the biological activity of human activated protein C without the necessity for activation.

The light and heavy chains of bovine protein C have been sequenced (Fernlund and Stenflo, J. Biol. Chem. 257: 12170–12179, 1982; and Stenflo and Fernlund, J. Biol. Chem. 257: 12180–12190, 1982). Isolation and characterization of human protein C have been described by Kisiel, J. Clin. Invest. 64: 761–769, 1979. The anticoagulant activities of both the human and bovine enzymes were found to be highly species specific. Species specificity is believed to be mediated by protein S (Walker, Thromb. Res. 22: 321–327, 1981). However, the human and bovine proteins show considerable overall structural homology to each other and to other vitamin K-dependent plasma proteins, including prothrombin, factor VII, factor IX, and factor X. Similarities include the presence of the Gla residues in the light chain and the active site serine in the heavy chain, as well as other amino acid sequence homology in the aminoterminal region of the light chain.

Within the present invention, a λgt11 cDNA library was prepared from human liver mRNA. This library was then screened with 125I labeled antibody to human protein C. Antibody-reactive clones were further analyzed for the synthesis of a fusion protein of β-galactosidase and protein C in the λgt11 vector.

One of the clones gave a strong signal with the antibody probe and was found to contain an insert of approximately 1400 bp. DNA sequence analysis of the DNA insert revealed a predicted amino acid sequence which shows a high degree of homology to major portions of the bovine protein C, as determined by Fernlund and Stenflo (J. Biol. Chem. 257: 12170–12179; J. Biol. Chem. 257: 12180–12190).

The DNA insert contained the majority of the coding region for protein C beginning with amino acid 64 of the light chain, including the entire heavy chain coding region, and proceeding to the termination codon. Further, following the stop codon of the heavy chain, there were 294 base pairs of 3' noncoding sequence and a poly (A) tail of 9 base pairs. The processing or polyadenylation signal A-A-T-A-A-A was present 13 base pairs upstream from the poly (A) tail in this cDNA insert. This sequence was one of two potential polyadenylation sites.

The cDNA sequence also contained the dipeptide Lys-Arg at position 156–157, which separates the light chain from the heavy chain and is removed during processing by proteolytic cleavage resulting in secretion of the two-chain molecule. Upon activation of the two-chain molecule by thrombin, the heavy chain of human protein C is cleaved between arginine-169 and leucine-170, releasing the activation peptide (FIG. 2).

By a similar method, a second cDNA which lacked the coding sequence for the pre-pro peptide and the first 23 amino acids of protein C was isolated. Using this cDNA as a hybridization probe, the remainder of the coding sequence was obtained from a human genomic DNA library in Charon 4A (Foster et al., Proc. Natl. Acad. Sci. USA 82: 4673–4677, 1985). Three different λ Charon 4A phage were isolated that contained overlapping inserts for the protein C gene.

Figure 3:
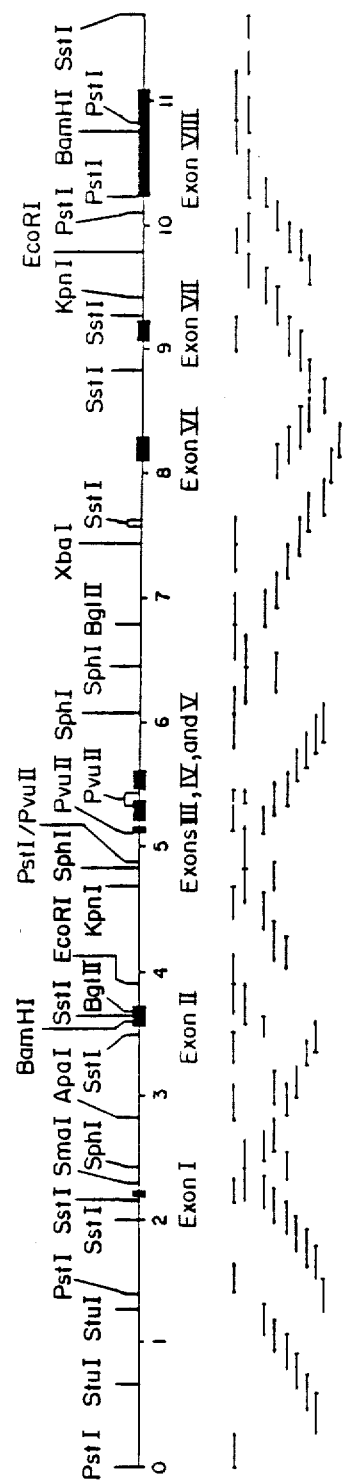
FIG. 3 illustrates a restriction enzyme map of the genomic DNA coding for human protein C. Numbers below the line indicate length in kilobases (kb).

The positions of exons on the three phage clones were determined by Southern blot hybridization of digests of these clones with probes made from the 1400 bp cDNA described above. The genomic DNA inserts in these clones were mapped by single and double restriction enzyme digestion followed by agarose gel electrophoresis, Southern blotting, and hybridization to radiolabeled 5' and 3' probes derived from the cDNA for human protein C, as shown in FIG. 3.

Figure 4:
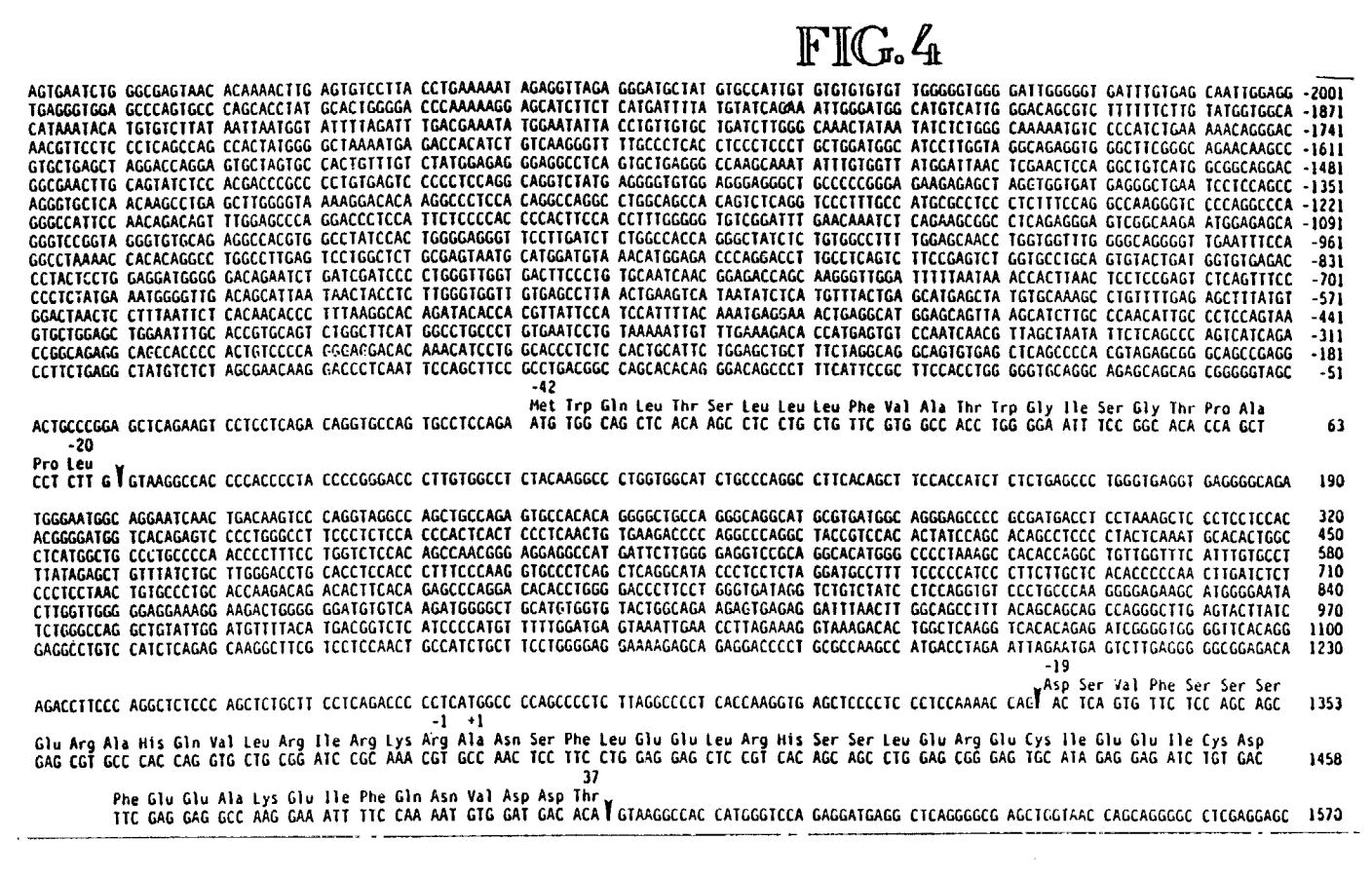
Figure 4:
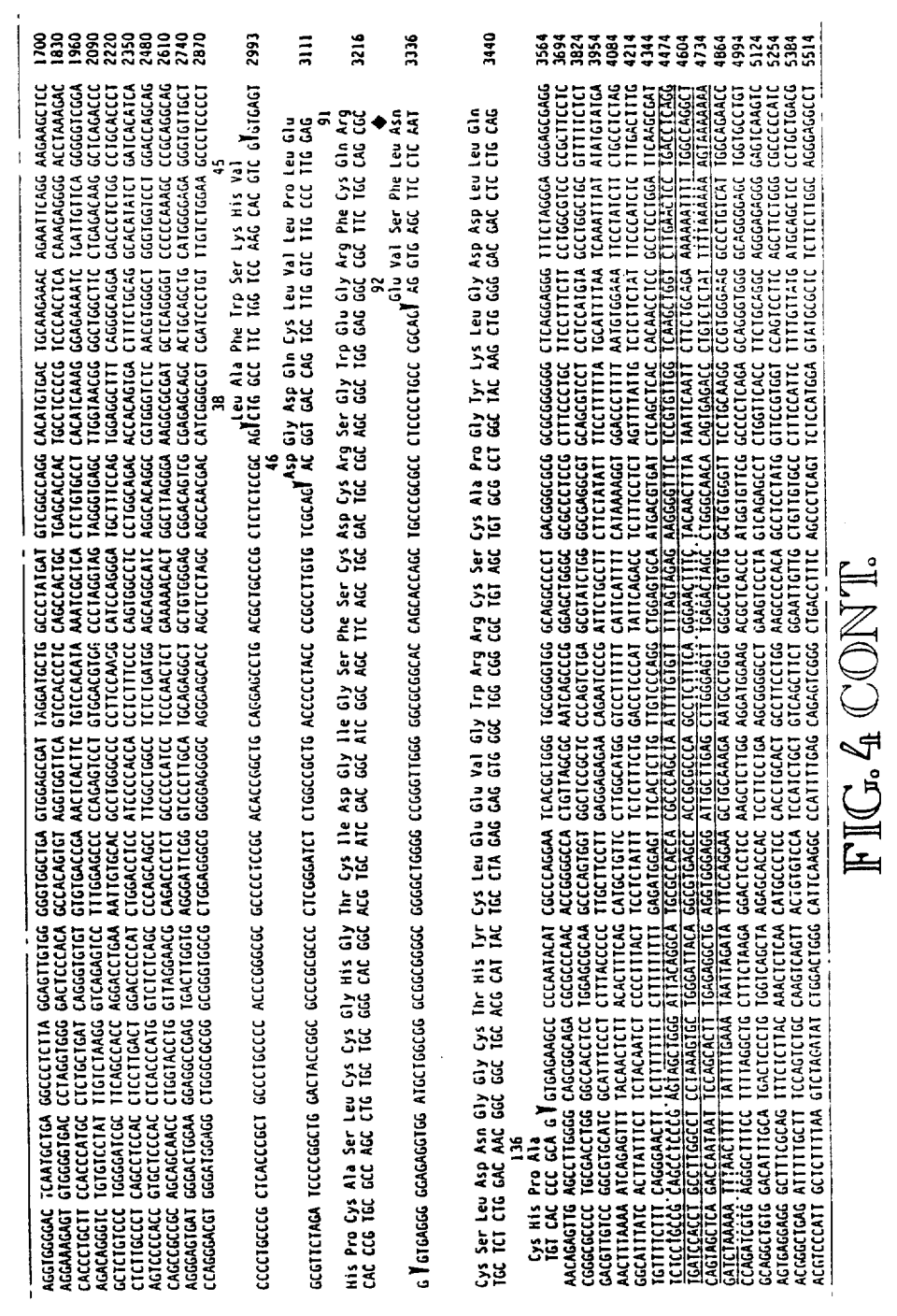
Figure 4:
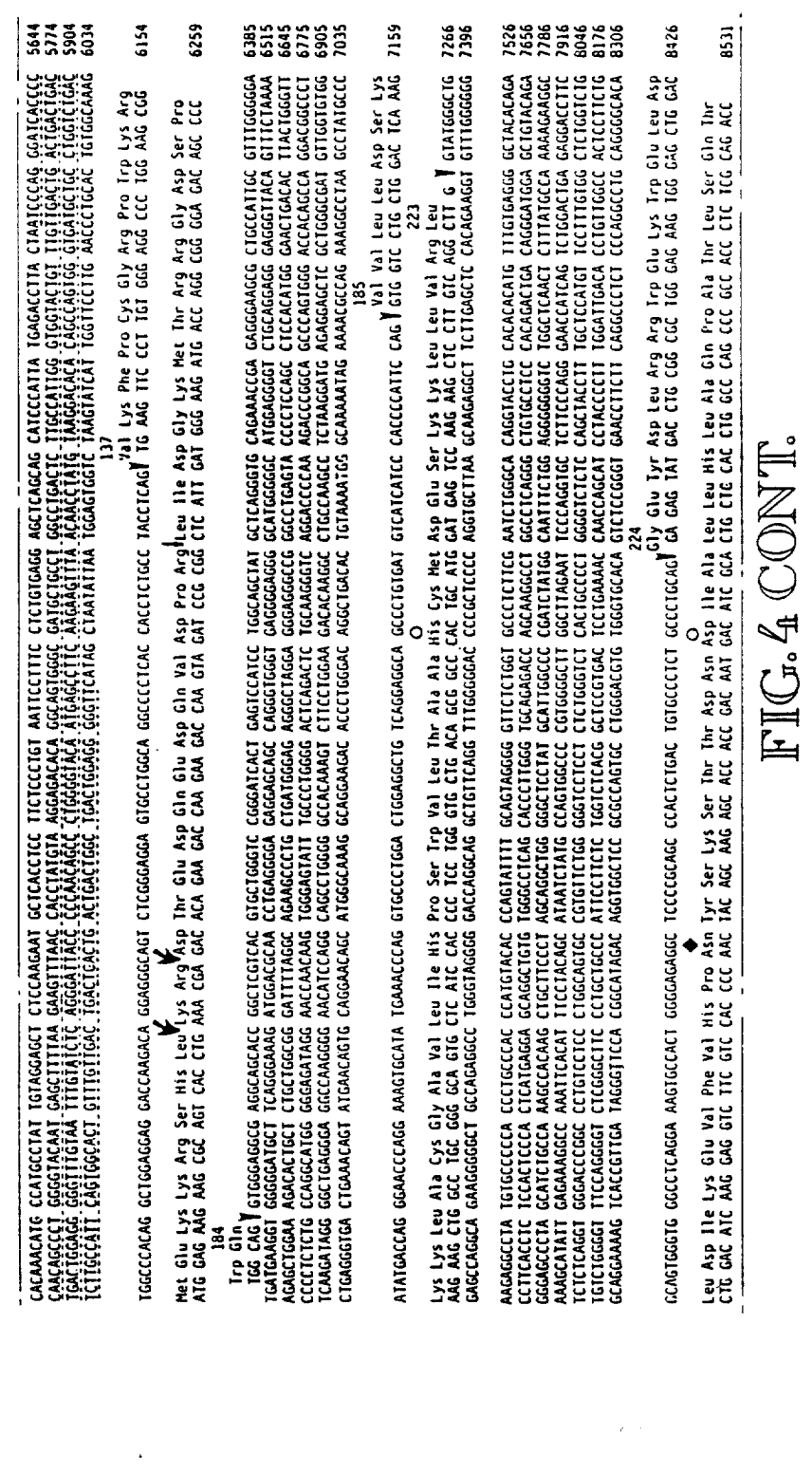
Figure 4:
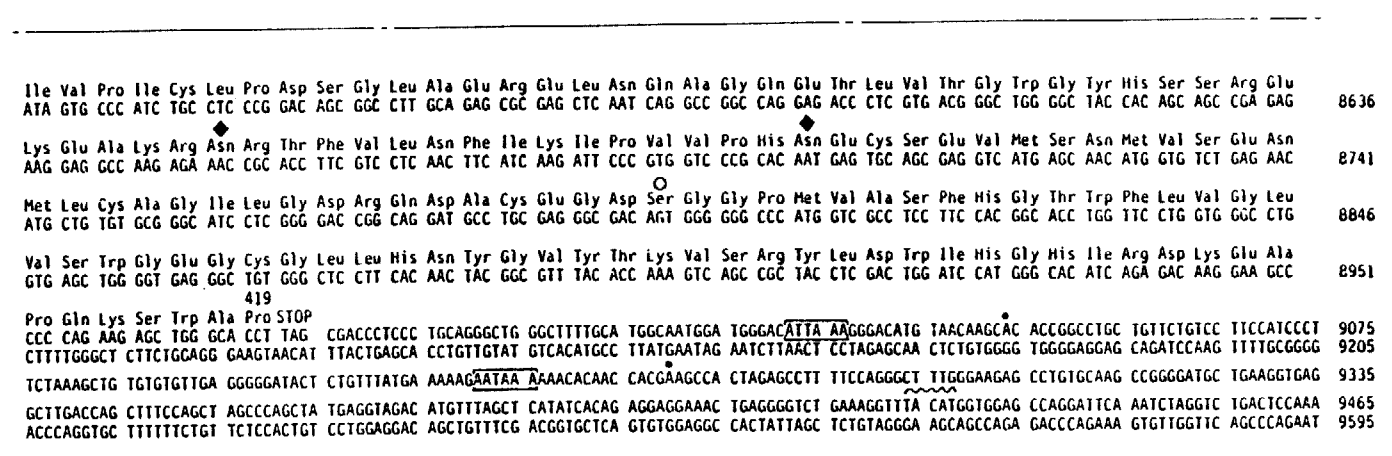

DNA sequencing studies were performed using the dideoxy chain-termination method. As shown in FIG. 4, the nucleotide sequence for the gene for human protein C spans approximately 11 kb of DNA. These studies further revealed a potential pre-pro peptide of 42 amino acids. The pre-pro sequence is cleaved by a signal peptidase following the Gly residue at position −25. Processing to the mature protein involves additional proteolytic cleavage following residue −1 to remove the amino-terminal propeptide, and at residues 155 and 157 to remove the Lys-Arg dipeptide which connects the light and heavy chains. This final processing yields a light chain of 155 amino acids and a heavy chain of 262 amino acids.

The protein C gene is composed of eight exons ranging in size from 25 to 885 nucleotides, and seven introns ranging in size from 92 to 2668 nucleotides. Exon I and a portion of exon II code for the 42 amino acid pre-pro peptide. The remaining portion of exon II, exon III, exon IV, exon V, and a portion of exon VI code for the light chain of protein C. The remaining portion of exon VI, exon VII, and exon VIII code for the heavy chain of protein C. The amino acid and DNA sequences for a cDNA coding for human protein C are shown in FIG. 2.

The introns in the gene for protein C are located primarily between various functional domains. Exon II spans the highly conserved region of the pre-pro peptide and the gamma-carboxyglutamic acid (Gla) domain. Exon III includes a stretch of eight amino acids which connect the Gla and growth factor domains. Exons IV and V each represent a potential growth factor domain, while exon VI covers a connecting region which includes the activation peptide. Exons VII and VIII cover the catalytic domain typical of all serine proteases.

Figure 5:
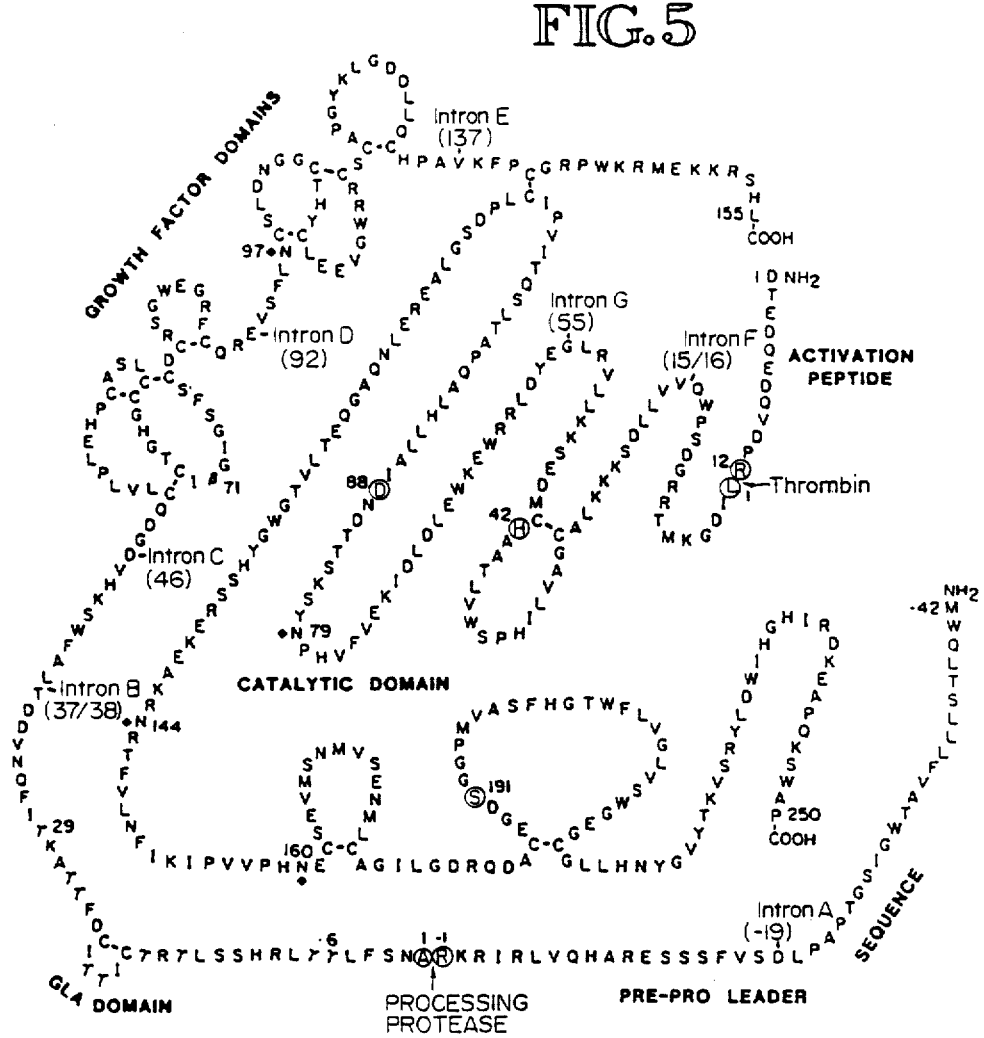
FIG. 5 illustrates a schematic two-dimensional model for the structure of human protein C.

The amino acid sequence and tentative structure for human pre-pro protein C are shown in FIG. 5. Protein C is shown without the Lys-Arg dipeptide, which connects the light and heavy chains. The location of the seven introns (A through G) is indicated by solid bars. Amino acids flanking known proteolytic cleavage sites are circled. ◊ designates potential carbohydrate binding sites. The first amino acid in the light chain, activation peptide, and heavy chain start with number 1. This numbering differs from that shown in FIGS. 2 and 4.

Carbohydrate attachment sites are located at residue 97 in the light chain and residues 79, 144, and 160 in the heavy chain, according to the numbering scheme of FIG. 5. The carbohydrate moiety is covalently linked to Asn. In the majority of instances, the carbohydrate attachment environment can be represented by Asn-X-Ser or Asn-X-Thr, where X=any amino acid.

As noted above, protein C plays a regulatory role in the coagulation process. The catalytic domain, encoded by exons VII and VIII, possesses serine protease activity which specifically cleaves certain plasma proteins (i.e., factors Va and VIIIa), resulting in their activation or deactivation. As a result of this selective proteolysis, protein C displays anticoagulant and fibrinolytic activities.

Due to the presence of intervening sequences in the genomic clone, merely joining the genomic and cDNA sequences to provide a complete coding sequence is not sufficient for constructing an acceptable expression unit. It is therefore necessary to delete these intervening sequences for reasons more fully described below if a genomic clone is used to construct the expression unit.

The 5' coding region may also be obtained by alternative methods and consequently eliminate the need to delete intervening sequences. The 5' coding region may be obtained by using probes derived from the existing cDNA or genomic clones to probe additional libraries. By this method, a full-length cDNA was isolated. Furthermore, the amino-terminal portions of the vitamin K-dependent plasma proteins are responsible for their respective calcium binding activities. It has been found that, as a result of this functional homology, the calcium binding domains of these molecules may be interchanged and still retain the activity specific to the catalytic domain of the resultant molecule. For example, as described in U.S. patent application Ser. No. 724,311, filed Apr. 17, 1985, the amino-terminal portion (calcium binding domain) of factor IX may be joined to factor VII at amino acid 36 to produce a protein having the activity of factor VII. Factor VII, factor IX, factor X, prothrombin, and protein S share this amino-terminal sequence homology with protein C. Consequently, a cloned sequence comprising the 5'-coding region of the gene for any of these proteins might be substituted for the corresponding sequence of the protein C gene. Additionally, suitable coding sequences may be synthesized based on the known amino acid sequences of several of the vitamin K-dependent plasma proteins or on the sequence of the genomic protein C exons disclosed herein. Techniques for producing synthetic nucleotide sequences are well known in the art. For example, a set of overlapping oligonucleotides may be synthesized and annealed in pairs to yield double-stranded fragments with overlapping cohesive termini. These fragments are then ligated as any restriction fragments would be. The resultant synthetic fragment is then ligated to the cDNA at a convenient restriction site. The junction sequence may be modified as necessary by oligonucleotide-directed mutagenesis.

When clones representing the entire coding sequence have been obtained, the appropriate regions may be joined, as necessary, to generate the desired coding sequence. Fragments obtained from one or more libraries are cut with appropriate restriction endonucleases and joined together enzymatically in the proper orientation. Depending on the fragments and the particular restriction endonucleases chosen, it may be necessary to remove unwanted DNA sequences through a "loop out" process of deletion mutagenesis or through a combination of restriction endonuclease cleavage and mutagenesis. The sequence so obtained should preferably be in the form of a continuous open reading frame, that is, that it lack the intervening sequences (introns) generally found in higher eukaryotic genes. The presence of introns in cloned genes may lead to aberrant splicing of messenger RNA and/or reduced efficiency of gene expression or instability upon amplification when the gene sequence is introduced into a mammalian host cell. It is preferred that this coding sequence further encode a pre-pro peptide in order to facilitate proper processing and secretion of the protein C produced according to the present invention. The pre-pro peptide may be that of protein C or another secreted protein, such as factor IX, factor VII, or prothrombin.

Under some circumstances, it may be desirable to produce activated protein C directly, thereby removing the need to activate the protein product either in vitro or in vivo. The cleavage sites involved in the maturation and activation of protein C are known (Foster and Davie, ibid). A sequence encoding APC may be constructed by deleting the region encoding the activation peptide through oligonucleotide-directed deletion mutagenesis. The resultant protein will then become activated by removal of the Lys-Arg dipeptide during normal proteolytic processing in the secretion pathway of the host cell. It has been found that proteins encoded by such a sequence are properly processed by the host cells, resulting in secretion of activated protein C.

In order to enhance the proteolytic processing involved in the maturation of the recombinant protein C to the two-chain form, it may be desirable to modify the amino acid sequence around the processing site. As previously noted, this maturation process involves the removal of the dipeptide Lys-Arg (amino acids 156–157) (Foster and Davie, *Proc. Natl. Acad. Sci. USA* 81: 4766–4770, 1984). The vitamin K-dependent protein factor X comprises the sequence Arg-Arg-Lys-Arg at the cleavage site between the light and heavy chains (Leytus et al., *Proc. Natl. Acad. Sci. USA* 81: 3699–3702, 1984). By the process of oligonucleotide-directed mutagenesis, two Arg codons may be inserted into the protein C sequence immediately 5' to the codon 156. This modification can be used in producing wild-type protein C or activated protein C.

The coding sequence for protein C or activated protein C is then inserted into a suitable expression vector which is, in turn, used to transfect a mammalian cell line. Expression vectors for use in carrying out the present invention will comprise a promotor capable of directing the transcription of a foreign gene introduced into a mammalian cell. Viral promoters are preferred due to their efficiency in directing transcription. A particularly preferred promotor is the major late promoter from adenovirus 2. Such expression vectors will also preferably contain a set of RNA splice sites located downstream from the promoter and upstream from the insertion site for the protein C sequence or within the protein C sequence itself. Preferred RNA splice sites may be obtained from adenovirus and/or immunoglobulin genes. Also contained in the expression vectors is a polyadenylation signal, located downstream of the insertion site. Viral polyadenylation signals are particularly preferred, such as the early or late polyadenylation signals from SV40 or the polyadenylation signal from the adenovirus 5 Elb region. In a particularly preferred embodiment, the expression vector also comprises a noncoding viral leader sequence, such as the adenovirus 2 tripartite leader, located between the promoter and the RNA splice sites. Preferred vectors may also include enhancer sequences, such as the SV40 enhancer and the sequences encoding the adenovirus VA RNAs.

Cloned gene sequences may then be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973). A precipitate is formed of the DNA and calcium phosphate, and this precipitate is applied to the cells. Some of the cells take up the DNA and maintain it inside the cell for several days. A small fraction of these cells (typically $10^{-4}$) integrate the DNA into the genome. In order to identify these integrants, a gene that confers a selectable phenotype (a selectable marker) is generally introduced into the cells along with the gene of interest. Preferred selectable markers include genes that confer resistance to drugs, such as neomycin, hygromycin, and methotrexate. Selectable markers may be introduced into the cell on a separate plasmid at the same time as the gene of interest, or they may be introduced on the same plasmid. If on the same plasmid, the selectable marker and the gene of interest may be under the control of different promoters or the same promoter. In one embodiment, the selectable marker is placed on the same plasmid with the sequence encoding protein C such that both sequences are controlled by the same promoter, an arrangement known as a dicistronic message. Constructs of this type are known in the art (for example, European Patent Office publication 117,058). It may also be advantageous to add additional DNA, known as "carrier DNA," to the mixture which is introduced into the cells. After the cells have taken up the DNA, they are allowed to grow for a period of time, typically 1-2 days, to begin expressing the gene of interest. Drug selection is then applied to select for the growth of cells which are expressing the selectable marker in a stable fashion. Clones of such cells may be screened for expression of protein C.

Preferred mammalian cell lines for use in the present invention include the COS, BHK and 293 cell lines. The 293 cell line (ATCC CRL 1573; Graham et al., *J. Gen. Virol.* 36: 59-72, 1977) is particularly preferred, due to its ability to efficiently process protein C to the two-chain form. This cell line is transformed with human adenovirus 5 DNA and has the Ad5 ElA gene integrated into its genome. Preferred expression vectors for use with 293 cells will include an adenovirus promoter. Neomycin resistance is a preferred selectable marker for use in 293 cells.

The copy number of the integrated gene sequence may be increased through amplification by using certain selectable markers (e.g., dihydrofolate reductase, which confers resistance to methotrexate). The selectable marker is introduced into the cells along with the gene of interest, and drug selection is applied. The drug concentration is then increased in a step-wise manner, with selection of resistant cells at each step. By selecting for increased copy number of cloned sequences, expression levels of the encoded protein may be substantially increased.

Protein C produced according to the present invention is preferably purified, as by affinity chromatography on an anti-protein C antibody column. Additional purification of the column eluate may be achieved by conventional chemical purification means, such as high-performance liquid chromatography (HPLC).

Protein C produced according to the present invention may be activated by removal of the activation peptide from the amino terminus of the heavy chain. Activation may be achieved using α-thrombin (Marlar et al., *Blood* 59: 1067-1072, 1982), trypsin (Marlar et al., ibid), Russell's viper venom factor X activator (Kisiel, ibid) or the commercially available activator Protac C (American Diagnostica).

To summarize the examples which follow, Example 1 describes the cloning of DNA sequences encoding human protein C. Example 2 describes the construction of a full-length coding sequence for protein C from the sequences isolated in Example 1. Example 3 describes the construction of expression vectors for the protein C DNA. Example 4 describes the production of protein C using transfected mammalian cells. Example 5 describes a full-length cDNA encoding protein C and its expression in transfected mammalian cells. Example 6 describes the production of activated protein C in BHK and 293 cells. Example 7 describes the use of the Factor VII pre-pro peptide to secrete protein C from transfected cells.

EXAMPLES

Restriction endonucleases and other DNA modification enzymes (e.g., T4 polynucleotide kinase, calf alkaline phosphatase, Klenow DNA polymerase, T4 polynucleotide ligase) were obtained from Bethesda Research Laboratories (BRL) and New England Biolabs and are used as directed by the manufacturer, unless otherwise noted.

Oligonucleotides may be synthesized on an Applied Biosystems Model 380 A DNA synthesizer and purified by polyacrylamide gel electrophoresis on denaturing gels. *E. coli* cells may be transformed as described by Maniatis et al. (*Molecular Cloning: A Laboratory Manual*, Cold Spring Harbor Laboratory, 1982). M13 and pUC cloning vectors and host strains were obtained from BRL.

EXAMPLE 1

Cloning of DNA Sequences Encoding Human Protein C

A cDNA coding for a portion of human protein C was prepared as described by Foster and Davie (ibid). Briefly, a λgt11 cDNA library was prepared from human liver mRNA by conventional methods. Clones were screened using 125I-labeled affinity-purified antibody to human protein C, and phage were prepared from positive clones by the plate lysate method (Maniatis et al., ibid), followed by banding on a cesium chloride gradient. The cDNA inserts were removed using Eco RI and subcloned into plasmid pUC9 (Vieira and Messing, *Gene* 19: 259–268, 1982). Restriction fragments were subcloned in the phage vectors M13mp10 and m13mp11 (Messing, *Meth. in Enzymology* 101: 20–77, 1983) and sequenced by the dideoxy method (Sanger et al., *Proc. Natl. Acad. Sci. USA* 74: 5463–5467, 1977). A clone was selected which contained DNA corresponding to the known sequence of human protein C (Kisiel, ibid) and encoded protein C beginning at amino acid 64 of the light chain and extending through the heavy chain and into the 3' non-coding region. This clone was designated λHC1375. A second cDNA clone coding for protein C from amino acid 24 was identified. The insert from this clone was subcloned into pUC9 and the plasmid designated pHCλ6L (FIG. 1). This clone encodes a major portion of protein C, including the heavy chain coding region, termination codon, and 3' non-coding region.

The cDNA insert from λHC1375 was nick translated using α-$^{32}$P dNTP's and used to probe a human genomic library in phage λ Charon 4A (Maniatis et al., *Cell* 15: 687–702, 1978) using the plaque hybridization procedure of Benton and Davis (*Science* 196: 181–182, 1977) as modified by Woo (*Meth. in Enzymology* 68: 381–395, 1979). Positive clones were isolated and plaque-purified (Foster et al., *Proc. Natl. Acad. Sci. USA* 82: 4673–4677, 1985, herein incorporated by reference). Phage DNA prepared from positive clones (Silhavy et al., in *Experiments with Gene Fusion*, Cold Spring Harbor Laboratory, 1984) was digested with Eco RI or Bgl II and the genomic inserts purified and subcloned in pUC9. Insert restriction fragments were subcloned into M13 vectors and sequenced to confirm their identity and establish the DNA sequence of the entire gene.

The cDNA insert of pHCλ6L was nick translated and used to probe the phage λ C 4A library. One genomic clone was identified which hybridized to probes made from the 5' and 3' ends of the cDNA. This phage clone was digested with Eco RI and a 4.4 kb fragment, corresponding to the 5' end of the protein C gene, was subcloned into pUC9. The resultant recombinant plasmid was designated pHCR4.4. Complete DNA sequence analysis revealed that the insert in pHCR4.4 comprised two exons of 70 and 167 base pairs separated by an intron of 1263 bp. The first exon encodes amino acids −42 to −19; the second encodes amino acids −19 to 37. Sequence analysis confirmed the DNA sequence of the entire protein C gene.

As noted above, it is then necessary to remove the intron in order to use a genomic clone to construct an acceptable coding sequence for use within the present invention.

EXAMPLE 2

Construction of a Full-Length Coding Sequence for Protein C

A full-length coding sequence for Protein C, including the pre-pro peptide, is constructed by joining the appropriate fragments of the cDNA and genomic clones. This is accomplished by removing the intron from the genomic clone (pHCR4.4) and joining the fused exons to the cDNA (from pHCλ6L) at convenient restriction sites. The desired genomic:cDNA junction is then generated by looping out unwanted sequences by oligonucleotide-directed deletion mutagenesis.

Figure 6:
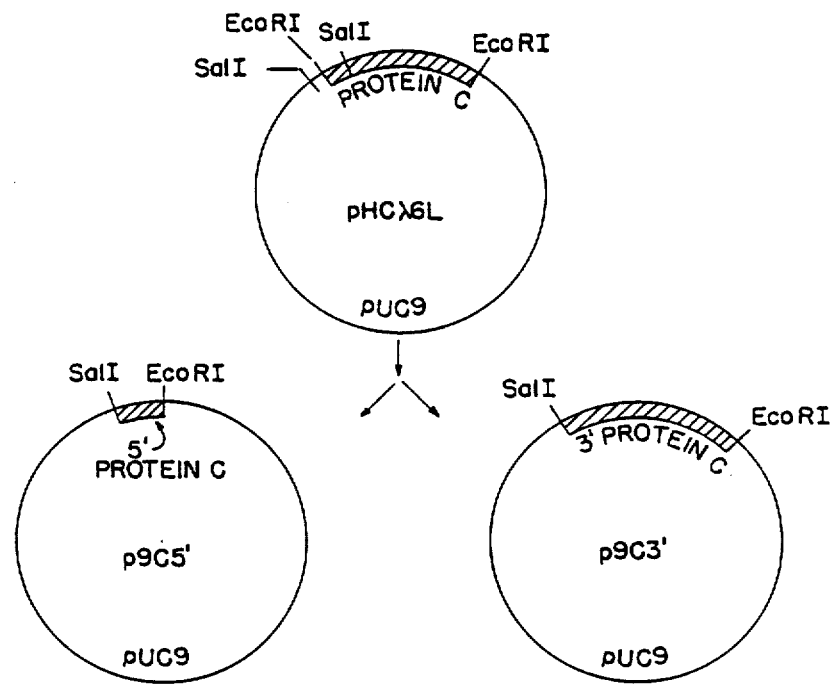
FIG. 6 illustrates the subcloning of the 5' and 3' portions of a protein C partial cDNA clone.

Plasmid pHCλ6L contains the protein C partial cDNA cloned in the Eco RI site of pUC9 (FIG. 1). The cDNA insert is subcloned in two fragments to prepare it for joining to the 5'-most coding region from the genomic clone. Plasmid pHCλ6L is digested with Eco RI and Sal I, and the reaction mixture is then extracted with phenol and CHCl$_3$ and ethanol-precipitated. The resulting DNA fragments are resuspended in ligation buffer, and T$_4$ DNA ligase is added. The ligation mixture is incubated at 15° C. for 14 hours. An aliquot of the ligation mix is used to transform *E. coli* JM83, and the cells are plated on LB agar containing X-gal. White colonies are selected, and plasmid DNA is prepared. The DNA is analyzed by restriction enzyme digestion to identify clones containing the 3' portion of the cDNA (ca. 1450 bp insert) and the 5' portion of the cDNA (ca. 65 bp insert). These clones are designated p9C3' and p9C5', respectively (FIG. 6).

The 5' coding region missing from the cDNA is contained in exons I and II of the genomic clone pHCR4.4. This plasmid contains an insert of approximately 4400 base pairs and terminates on its 3' end at an Eco RI site located in intron B.

To remove the coding sequences from pHCR4.4, the plasmid is digested with PstI and Eco RI and the resulting fragments separated by electrophoresis in an agarose gel. The ca.2540 bp fragment containing exons I and II is isolated from the gel and extracted with CTAB (Langridge, et al., *Analyt. Biochem.* 103: 264, 1980). This fragment, designated 5'P-R, is subcloned into pUC9 to produce plasmid p5'P-R (FIG. 7).

Figure 7:
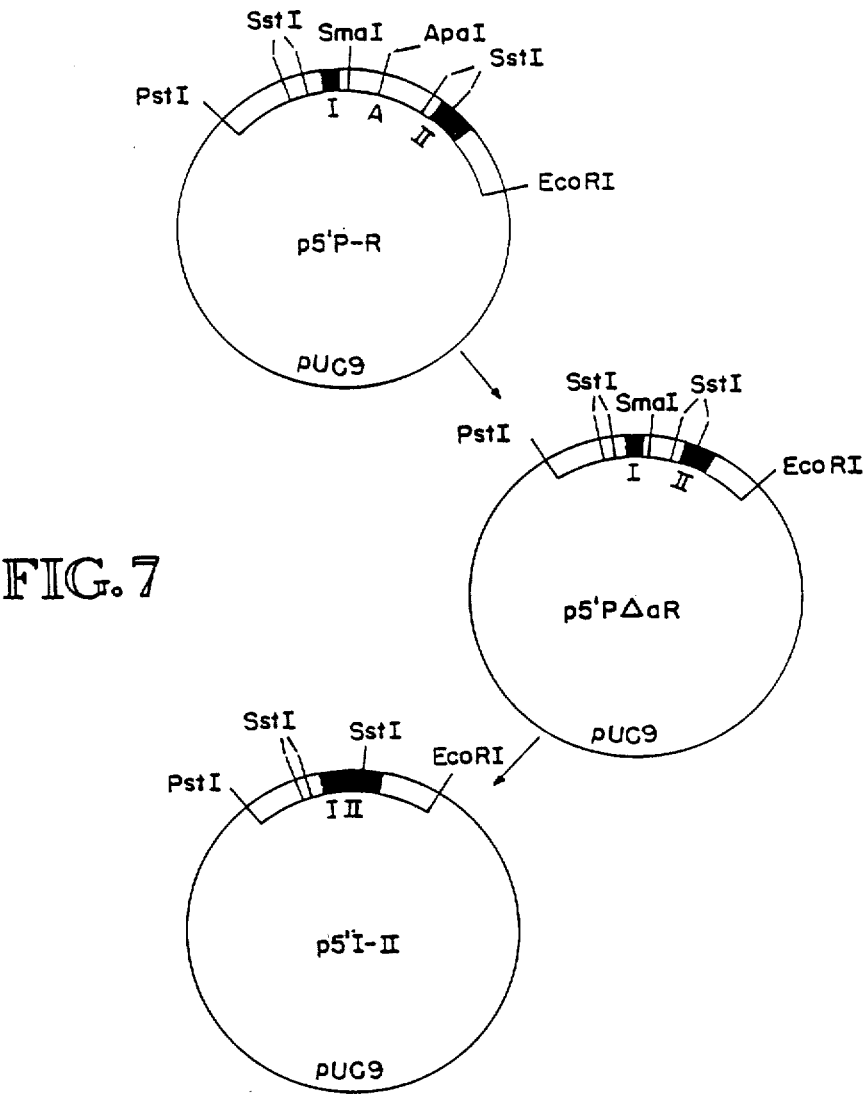
FIG. 7 illustrates the removal of intron A from the genomic clone, resulting in the fusion of exons I and II.

The intron in p5'P-R (designated intron A), is removed in a two-step process (FIG. 7). The plasmid is digested with Apa I, which cleaves at a unique site in the intron and leaves 3' overhanging ends. The linearized plasmid is then treated with Bal 31 exonuclease or T$_4$ polymerase to remove approximately 400 bp from each end and the resultant fragment ends are blunted with S1 nuclease. The linearized plasmid is recircularized with ligase and used to transform *E. coli* JM83. Plasmid DNA is extracted and analyzed for the presence of the Sma I and Sst I restriction sites in intron A, and a plasmid having a Sma I-SstI fragment reduced to 300–400 bp is chosen and designated p5'PΔaR.

The remainder of intron A is removed by oligonucleotide-directed deletion mutagenesis, essentially as described by Zoller and Smith (*Manual for Advanced Techniques in Molecular Cloning Course*, Cold Spring Harbor Laboratory, 1983) for the two-primer method. p5'PΔaR is digested with Pst I and Eco RI, and the protein C fragment is subcloned into Pst I+Eco RI-digested M13mp9. Plus strand phage DNA is prepared as template and annealed to oligonucleotide mut-1 (Table 1). This mutagenic oligonucleotide comprises sequences complementary to the exon I and II sequences to be joined. The M13 universal sequencing primer is annealed 3' to mut-1 on the same template. The primers are extended using DNA polymerase (Klenow fragment) and nucleoside triphosphates in the presence of $T_4$ ligase. The resulting duplex DNA circles are transformed into *E. coli* JM103 and the resulting plaques screened under stringent hybridization conditions using the $^{32}$P-labeled mutagenic oligonucleotide as probe. DNA from positive plaques is isolated and sequenced using oligonucleotide primer-1 (Table 1), which primes in exon II, allowing the determination of the DNA sequence across the deletion junction. A molecule having the correct inframe fusion of exons I and II is selected. The PstI-EcoRI fragment is isolated from the M13 replicative form by restriction endonuclease digestion and agarose gel electrophoresis and is subcloned into pUC9 to produce plasmid p5'I-II (FIG. 7).

Figure 8:
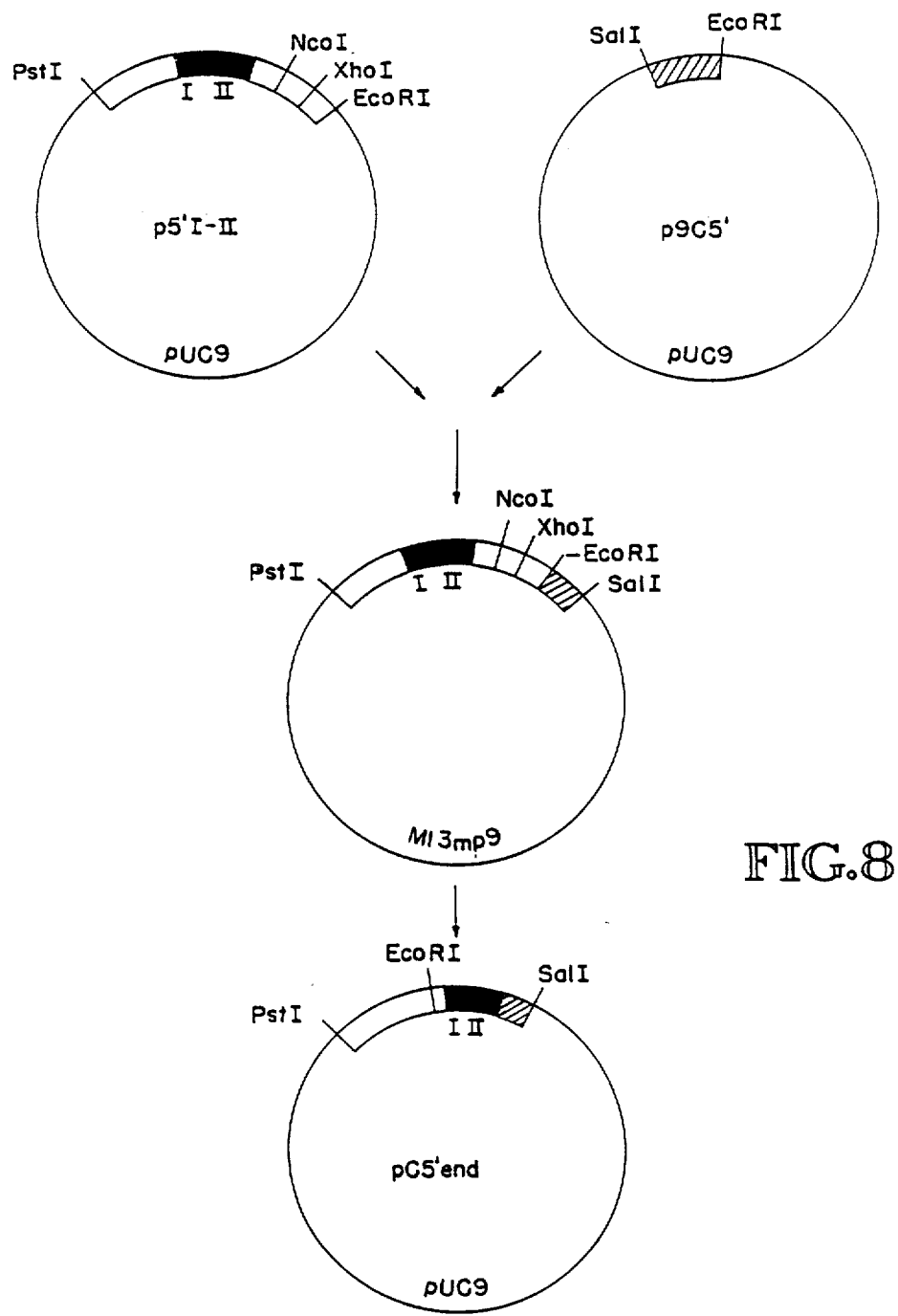
FIG. 8 illustrates the fusion of exons I and II to the 5'-most portion of the cDNA insert of FIG. 1.

Referring to FIG. 8, to join the 5' coding region to the cDNA, the ca. 1277 bp Pst I-Eco RI fragment of p5'I-II is isolated from a Pst I+Eco RI digest of the plasmid and purified by agarose gel electrophoresis. The 65 bp 5'-most cDNA fragment is isolated from a Sal I+Eco RI digest of p9C5' and purified by electrophoresis on an acrylamide gel. The two fragments are ligated at their Eco RI termini, and the resulting ca. 1330 bp Pst I-Sal I fragment is subcloned into Pst I+Sal I-digested M13mp9 (FIG. 8). Plus strand phage DNA is prepared as template for oligonucleotide-directed deletion mutagenesis. Oligonucleotide mut-2 (Table 1) is annealed to the template, and oligonucleotide mut-3 (Table 1) is annealed upstream as second primer. The primers are extended as described above. Oligonucleotide mut-2 directs the fusion of exon II sequences encoding amino acids 23–26 to the cDNA at codon 27. The second primer (mut-3) introduces an Eco RI site 35 bp upstream from the start of translation. The resulting phage are screened for the absence of Nco I and Xho I sites and for the presence of the introduced Eco RI site. Phage DNA showing the desired restriction pattern is sequenced using primer-2 (Table 1) to verify the presence of the correct junction between exon II and the cDNA. Phage DNA with the correct sequence is selected, and the Pst 1-Sal I fragment comprising the 5' coding region is isolated from the replicative form of the M13 recombinant phage. The fragment is purified by agarose gel electrophoresis and inserted into Pst I+Sal I-digested pUC9 to produce plasmid pC5'end.

Figure 9:
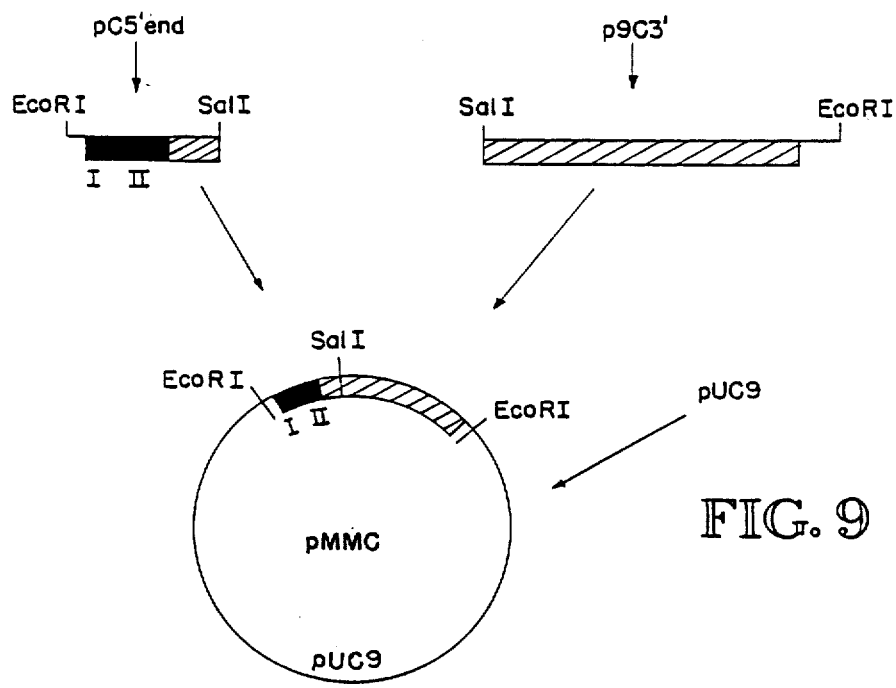
FIG. 9 illustrates the construction of a plasmid comprising the complete coding sequence for protein C.

Referring to FIG. 9, plasmid pC5'end is digested with EcoRI and Sal I, and the 5' protein C fragment is purified by agarose gel electrophoresis and extraction with CTAB. The remainder of the cDNA is isolated as a Sal I - Eco RI fragment from p9C3'. The two fragments are joined in a three-part ligation to Eco RI- digested pUC9. The ligation mixture is used to transform *E. coli* JM83, the cells are plated on LB+X-gal, and plasmid DNA is isolated from white colonies. The resultant plasmid is designated pMMC. It contains the complete coding sequence for human protein C on a ca. 1500 bp Eco RI fragment.

TABLE I

| Oligo-nucleotide | Sequence |
|---|---|
| mut-1 | 3'CGA GGA GAA CTG AGT CAC AA5' |
| mut-2 | 3'CTG AAG CTC CTC CGG TTC CTT TAA5' |
| mut-3 | 5'GGA GGA ATT CTG AGC3' |
| primer-1 | 5'TTT GCG GAT CCG CAG3' |

TABLE I-continued

| Oligo-nucleotide | Sequence |
|---|---|
| primer-2 | 5'CGA CGT GCT TGG ACC3' |

EXAMPLE 3

Construction of Expression Vectors for Protein C

The protein C-encoding insert is removed from pMMC as an Eco RI fragment and inserted into a suitable mammalian cell expression vector. An exemplary vector is pD7, comprising the SV40 enhancer and the adenovirus 2 major late promoter and tripartite leader.

Plasmid pD7 is generated from plasmid pDHFRIII (Berkner and Sharp, *Nuc. Acids Res.* 13: 841–857, 1985). The Pst I site immediately upstream from the DHFR sequence in pDHFRIII was converted to a Bcl I site by digesting 10 ug of plasmid with 5 units of Pst I for 10' at 37° C. in 100 ul buffer A (10 mM Tris pH 8, 10 mM $MgCl_2$, 6 mM NaCl, 7 mM $\beta$-MSH). The DNA was phenol extracted, EtOH precipitated, and resuspended in 40 ul buffer B (50 mM Tris pH 8, 7 mM $MgCl_2$, 7mM $\beta$-MSH) containing 10 mM dCTP and 16 units $T_4$ DNA polymerase and incubated at 12° C. for 60 minutes. Following EtOH precipitation, the DNA was ligated to 2.5 ug kinased Bcl I linkers in 14 ul buffer C (10 mM Tris pH 8, 10 mM $MgCl_2$, 1 mM DTT, 1.4 mM ATP) containing 400 units $T_4$ polynucleotide ligase for 12 hours at 12° C. Following phenol extraction and EtOH precipitation, the DNA was resuspended in 120 ul buffer D (75 mM KCl, 6 mM Tris pH 7.5, 10 mM $MgCl_2$, 1 mM DTT), digested with 80 units Bcl I for 60 minutes at 50° C., then electrophoresed through agarose. Form III plasmid DNA (10 ug) was isolated from the gel, and ligated in 10 ul buffer C containing 50 units $T_4$ polynucleotide ligase for 2 hours at 12° C., and used to transform *E. coli* HB101. Positive colonies were identified by rapid DNA preparation analysis, and plasmid DNA (designated pDHFR') prepared from positive colonies was transformed into dAM- *E. coli*.

Plasmid pD2' was then generated by cleaving pDHFR' (15 ug) and pSV40 (comprising Bam HI digested SV40 DNA cloned into the Bam HI site of pML-1) (25 ug) in 100 ul buffer D with 25 units Bcl I for 60 minutes at 50° C., followed by the addition of 50 units Bam HI and additional incubation at 37° C. for 60 minutes. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 ul buffer C containing 100 units $T_4$ polynucleotide ligase for 4 hours at 12° C., and the resulting construct (pD2') was used to transform *E. coli* RRI.

Plasmid pD2' was modified by deleting the "poison" sequences in the pBR 322 region (Lusky and Botchan, *Nature* 293: 79–81, 1981). Plasmids pD2' (6.6 ug) and pML-1 (Lusky and Botchan, ibid) (4 ug) were incubated in 50 ul buffer A with 10 units each Eco RI and Nru I for 2 hours at 37° C., followed by agarose gel electrophoresis. The 1.7 kb pD2' fragment and 1.8 kb pML-1 fragment were isolated and ligated together (50 ng each) in 20 ul buffer C containing 100 units $T_4$ polynucleotide ligase for 2 hours at 12° C., followed by transformation into *E. coli* HB101. Colonies containing the desired construct (designated pD2) were identified by rapid preparation analysis. Ten ug of pD2 were then digested with 20 units each Eco RI and Bgl II, in 50 ul buffer A for 2 hours at 37° C. The DNA was electrophoresed through agarose, and the desired 2.8 kb fragment (fragment C) comprising the pBR322, 3' splice site and poly A sequences was isolated.

To generate the remaining fragments used in constructing pD3, pDHFRIII was modified to convert the Sac II (Sst II) site into either a Hind III or Kpn I site. Ten ug pDHFRIII were digested with 20 units Sst II for 2 hours at 37° C., followed by phenol extraction and ethanol precipitation. Resuspended DNA was incubated in 100 ul buffer B containing 10 mM dCTP and 16 units T₄ DNA polymerase for 60 minutes at 12° C., phenol extracted, dialyzed, and ethanol precipitated. DNA (5 ug) was ligated with 50 ng kinased Hind III or Kpn I linkers in 20 ul buffer C containing 400 units T₄ DNA ligase for 10 hours at 12° C., phenol extracted, and ethanol precipitated. After resuspension in 50 ul buffer A, the resultant plasmids were digested with 50 units Hind III or Kpn I, as appropriate, and electrophoresed through agarose. Gel-isolated DNA (250 ng) was ligated in 30 ul buffer C containing 400 units T₄ DNA ligase for 4 hours at 12° C. and used to transform E. coli RRI. The resultant plasmids were designated pDHFRIII (Hind III) and pDHFRIII (Kpn I). A 700 bp Kpn I-Bgl II fragment (fragment A) was then purified from pDHFRIII (Kpn I) by digestion with Bgl II and Kpn I followed by agarose gel electrophoresis.

The SV40 enhancer sequence was inserted into pDHFRIII (Hind III) as follows: 50 ug SV40 DNA was incubated in 120 ul buffer A with 50 units Hind III for 2 hours at 37° C., and the Hind III C SV40 fragment (5089–968 bp) was gel purified. Plasmid pDHFRIII (Hind III) (10 ug) was treated with 250 ng calf intestinal phosphatase for 1 hour at 37° C., phenol extracted and ethanol precipitated. The linearized plasmid (50 ng) was ligated with 250 ng Hind III C SV40 in 16 ul buffer C for 3 hours at 12° C., using 200 units T₄ polynucleotide ligase, and transformed into E. coli HB101. A 700 base pair Eco RI-Kpn I fragment (fragment B) was then isolated from this plasmid.

For the final construction of pD3, fragments A and B (50 ng each) were ligated with 10 ng fragment C with 200 units T₄ polynucleotide ligase for 4 hours at 12° C., followed by transfection of E. coli RRI. Positive colonies were detected by rapid preparation analysis, and a largescale preparation of pD3 was made.

Figure 10:
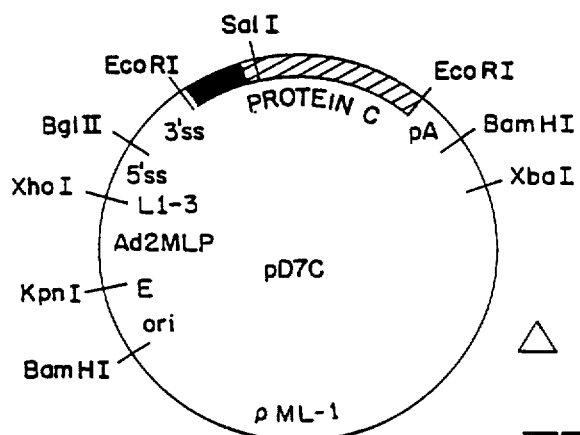
FIG. 10 illustrates the expression vector pD7C. Symbols used are ori, the adenovirus 5 0-1 map unit sequence; E, the SV40 enhancer; Ad2MLP, the adenovirus 2 major late promoter; L 1-3, the adenovirus 2 tripartite leader; 5'ss, 5' splice site; 3'ss, 3' splice site; pA, the SV40 early polyadenylation signal; and Δ, the deleted region of the pBR322 "poison" sequences.

Plasmid pD3 is modified to accept the insertion of the protein C sequence by converting the Bcl I insertion site to an Eco RI site. It is first necessary to remove the Eco RI site present in pD3 at the leftmost terminus of the adenovirus 5 0-1 map unit sequences by converting it to a Bam HI site via conventional linkering procedures. Briefly, the plasmid is digested with Eco RI and the linearized DNA treated with T₄ DNA polymerase and all four deoxynucleotide triphosphates to generate blunt termini. The plasmid is then ligated to octonucleotides comprising the Bam HI restriction site, the DNA digested with Bam HI to remove excess linkers, and the fragment comprising the mammalian cell expression sequences is cloned into the Bam HI site of pML-1. The resultant plasmid is transformed into E. coli HB101, and plasmid DNA is prepared and screened for the correct conversion. In a similar manner, the Bcl I site is converted to an Eco RI site using appropriate octonucleotide linkers. The resultant vector is known as pD7. The 1.5 kb protein C Eco RI fragment from pMMC is then inserted into the Eco RI site of pD7 to produce the expression vector pD7C (FIG. 10).

A vector enabling expression of the protein C sequence from a polycistronic message is constructed by using pD5, a plasmid similar to pD3 which contains a DHFR coding sequence lacking most of the 5' non-coding region. The DHFR sequence is further modified to reduce its binding affinity to methotrexate.

The vector pD5 is constructed by a method analogous to that described for pD3, and differs from pD3 only in that a Bam HI site is the site of insertion of heterologous DNAs, and that the Bcl I-Bam HI SV40 fragment containing the SV40 polyadenylation signal is in the late orientation.

The DHFR sequence is modified by first digesting pDHFRIII with Pst I and Sst I and isolating the 400 bp DHFR fragment. This is subcloned in an M13 phage vector and mutagenized as described by Simonsen and Levinson (Proc. Natl. Acad. Sci. USA 80: 2495–2499, 1983). Mutagenesis results in a single base pair change in the DHFR sequence. The altered fragment is then reinserted into pDHFRIII to produce plasmid pDHFR'III.

The 5' non-coding region of the DHFR sequence is then removed. Plasmid pDHFR'III is cleaved with Fnu 4HI, which cuts the plasmid at approximately 20 sites, then treated with T₄ DNA polymerase and all four deoxynucleotide triphosphates to generate blunt termini. Bam HI linkers are ligated to the ends, and the mixture digested with Bam HI and Nco I. A 0.6 kb Bam HI-Nco I fragment comprising the DHFR' cDNA is isolated. Plasmid pDHFRIII is digested with Nco I and Bam HI and the 0.2 kb fragment comprising the SV40 polyadenylation signal is isolated. The polyadenylation signal, in the early orientation, is then ligated to the DHFRr fragment. After digestion with Bam HI, the resultant Bam HI fragment is then inserted into the Bam HI site of pD5 and the ligation mixture used to transform E. coli HB101. plasmid DNA is prepared and screened by restriction endonuclease digestion. A plasmid having the DHFR' insert in the correct orientation for transcription from the Ad2 major late promoter is designated pD5(DHFR').

Figure 11:
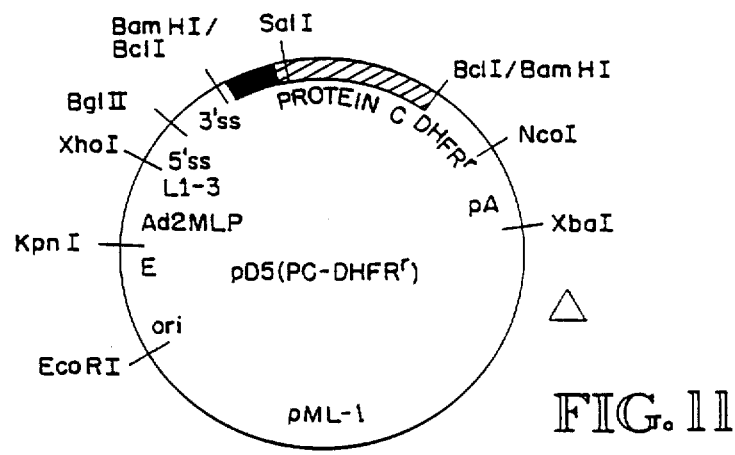
FIG. 11 illustrates the expression vector pD5(PC-DHFR'). DHFR' denotes the methotrexate resistant mutant dihydrofolate reductase gene sequence; pA denotes the SV40 late polyadenylation signal. Other symbols used are as described for FIG. 10.

To express protein C using plasmid pD5(DHFRr), pMMC is digested with Eco RI and the 1.5 kb protein C fragment is isolated. The Eco RI termini are converted to Bcl I termini by linkering. Plasmid pD5(DHFR') is partially digested with Bam HI to cleave it at the 5' end of the DHFR' sequence and is ligated to the protein C fragment. Plasmid DNA is screened for the proper orientation and insertion of the protein C fragment. The resultant vector, designated pD5(PC-DHFR'), is illustrated in FIG. 11.

EXAMPLE 4

Expression of Protein C in Transfected Mammalian Cells

Baby hamster kidney (BHK) cells (American Type Culture Collection accession number CCL10) are transfected with pD7C essentially as described (Wigler et al., Cell 14: 725, 1978; Corsaro and Pearson, Somatic Cell Genetics 7: 603, 1981; and Graham and Van der Eb, Virology 52: 456, 1973). The cells are grown at 37° C., 5% $CO_2$ in Dulbecco's medium (plus 10% heat-inactivated fetal calf serum and supplemented with glutamine and penicillin-streptomycin) in 60 mm tissue culture Petri dishes to a confluency of 20%. A total of 10 ug of DNA is used to transfect one 60 mm dish: 3.75 ug of pD7C, 1.25 ug of pKO-neo (Southern and Berg, *J. Mol. Appl. Genet* 1: 327–341, 1982) and 5 ug of salmon sperm DNA. The DNAs are precipitated in 0.3 M NaOAc, 75% ethanol, rinsed with 70% ethanol and redissolved in 20 ul 10 mM Tris-HCl pH8, 1 mM EDTA. The DNA is combined with 440 ul H$_2$O and 500 ul of 280 mM NaCl, 1.5 mM NaHPO$_4$, 12 mM dextrose, 50 mM HEPES pH 7.12. Sixty ul of 250 mM CaCl$_2$ are added dropwise to the above mixture and the solution let stand at room temperature for 30 minutes. The solution is then added to the cells and the cells returned to 37° C. for 4 hours. The medium is removed and 5 ml of 20% DMSO in Dulbecco's with serum are added for 2 minutes at room temperature. The dish is then washed rapidly with 2 changes of medium and incubated in fresh medium overnight. Twenty-four hours after the addition of the DNA, the medium is removed and selective medium (10 mg/ml of G418, 498 u/mg, Gibco, in Dulbecco's with serum) added. After approximately 10–13 days, individual clones, representing cells that have incorporated the pKO-neo gene and are thus resistant to G418, are transferred to 96-well plates and grown up for protein assays in Dulbecco's plus 10% fetal calf serum.

To assay for protein C, the medium is separated from the cells and cellular debris by centrifugation, and assayed for protein C polypeptide and biological activity. The cells are removed from the plates with trypsin, washed with fresh medium, centrifuged and frozen at −20° C. For assay, the cell pellets are thawed in PBS, pelleted, and resuspended in PBS containing 0.25% Triton X-100. Samples are diluted and assayed for polypeptide and activity.

The ELISA for protein C is done as follows: Two hundred microliters of antibody (monoclonal or polyclonal) against human protein C (5 ul/ml in 0.1 M Na$_2$CO$_3$ pH 9.6) are incubated in each well of a 96-well microtiter plate 2 hours at 37° C. The wells are then incubated with 220 ul of 1% bovine serum albumin (BSA) and 0.05% Tween 20 in PBS pH 7.2 for 2 hours at 37° C. The plates are rinsed with H$_2$O, air dried, and stored at 4° C. To assay samples, 200 ul samples are incubated 1 hour at room temperature in the antibody-coated wells. The wells are then rinsed four times with 200 ul PBS containing 0.05% Tween 20. The wells are then incubated for 1 hour at room temperature with 200 ul of an IgG fraction of rabbit polyclonal antiserum against protein C (5 ug/ml in PBS containing 1% BSA and 0.05% Tween 20). This is followed by incubation with goat anti-rabbit IgG coupled to alkaline phosphatase. The wells are then rinsed four times with PBS containing 0.05% Tween 20. To the wells are added 200 ul p-nitrophenyl phosphate (30 mg) dissolved in diethanolamine buffer (96 ml per liter) pH 9.8 containing 56 mg/1 MgCl$_2$. The enzyme reaction is done at 37° C. and the development of a yellow color is monitored at 405 nm using an ELISA plate reader.

Protein C biological activity is assayed by its ability to prolong the kaolin-cephalin clotting time of plasma following its activation by thrombin as described by Kisiel and Davie (*Meth. in Enzymology* 80: 320–332, 1981).

EXAMPLE 5

Expression of a Full-Length cDNA Encoding Protein C

A. Isolation of cDNA

A genomic fragment containing an exon corresponding to amino acids −42 to −19 of the pre-pro peptide (Exon 1 in FIG. 4) of protein C was isolated, nick translated, and used as a probe to screen a cDNA library constructed by the technique of Gubler and Hoffman (*Gene* 25: 263–269, 1983) using mRNA from HEPG2 cells. This cell line was derived from human hepatocytes and was previously shown to synthesize protein C (Fair and Bahnak, *Blood* 64: 194–204, 1984). Ten positive clones comprising cDNA inserted into the Eco RI site of phage λgt11 were isolated and screened with an oligonucleotide probe corresponding to the 5' noncoding region of the protein C gene. One clone was also positive with this probe and its entire nucleotide sequence was determined. The cDNA contained 70 bp of 5' untranslated sequence, the entire coding sequence for human prepro-protein C, and the entire 3' noncoding region corresponding to the second polyadenylation site (FIG. 2).

B. Expression Vector Construction

The expression of protein C cDNA was achieved in the vector pDX. This vector was derived from pD3 (described in Example 3 above) and pD3', a vector identical to pD3 except that the SV40 polyadenylation signal (i.e. the SV40 BamHI [2533 bp] to BclI [2770 bp] fragment) is in the late orientation. Thus, pD3' contains a Bam HI site as the site of gene insertion.

To generate pDX, the Eco RI site in pD3' was converted to a BclI site by Eco RI cleavage, incubation with S1 nuclease, and subsequent ligation with Bcl I linkers. DNA was prepared from a positively identified colony, and the 1.9 kb Xho I-Pst I fragment containing the altered restriction site was prepared via agarose gel electrophoresis. In a second modification, Bcl I-cleaved pD3 was ligated with kinased Eco RI-Bcl I adaptors (constructed from oligonucleotides ZC 525, 5'GGAATTCT3'; and ZC526, 5'GATCAGAATTCC3') in order to generate an Eco RI site as the position for inserting a gene into the expression vector. Positive colonies were identified by restriction endonuclease analysis, and DNA from this was used to isolate a 2.3 kb Xho I--Pst I fragment containing the modified restriction site. The two above-described DNA fragments were incubated together with T$_4$ DNA ligase, transformed into *E. coli* HB101 and positive colonies were identified by restriction analysis. A preparation of such DNA, termed pDX, was then made. This plasmid contains a unique Eco RI site for insertion of foreign genes.

Figure 12:
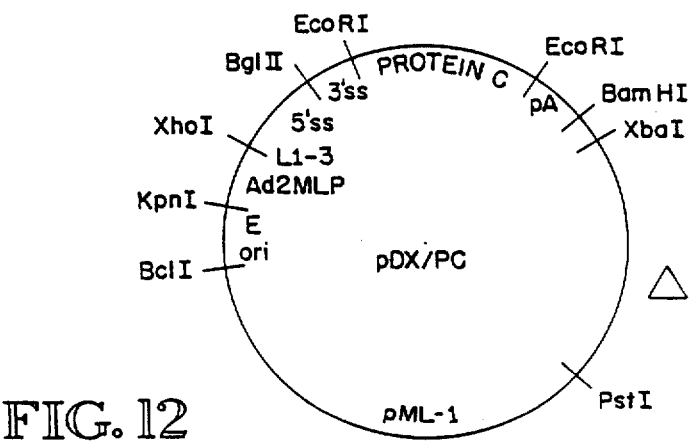
FIG. 12 illustrates the expression vector pDX/PC. Symbols used are as described for FIG. 11.

The protein C cDNA was then inserted into pDX as an Eco RI fragment. Recombinant plasmids were screened by restriction analysis to identify those having the protein C insert in the correct orientation with respect to the promoter elements and plasmid DNA (designated pDX/PC) was prepared from a correct clone (FIG. 12). Because the cDNA insert in pDX/PC contains an ATG codon in the 5' noncoding region (see FIG. 2), deletion mutagenesis was performed on the cDNA prior to transfection and expression experiments. Deletion of the three base pairs was performed according to standard procedures of oligonucleotidedirected mutagenesis. The pDX-based vector containing the modified cDNA was designated p594.

C. cDNA Expression

Plasmid p594 was transfected into COS, BHK and 293 cells by calcium phosphate precipitation. Four hours later, fresh culture media (supplemented with 5 ug/ml vitamin K) were added. At appropriate times (usually 48 or 72 hours), the culture media were harvested and the cells were collected and lysed.

The protein C secreted into the culture medium was assayed by ELISA using the same affinity-purified polyclonal antibody which was used in the initial identification of the cDNA clones. Results of the assays of COS and 293 cells (Table 2) showed that protein C was secreted from the transfected cells. It was found that 293 cells gave consistently higher levels of protein C than did COS cells.

To assess the extent of gamma-carboxylation of the recombinant protein, samples of the culture media were subjected to barium citrate precipitation, a process which selectively precipitates only gamma-carboxylated proteins from plasma (Bajaj et al., *J. Biol. Chem.* 256: 253–259, 1981). Over 70% of the protein C antigenic material could be precipitated with barium citrate.

The recombinant protein C was assayed for anticoagulant activity by measuring its ability to prolong coagulation. Dialyzed media samples were treated with Protac C (American Diagnostica) to activate the protein C. The samples were then added to an in vitro clotting assay (Sugo et al., *J. Biol. Chem.* 260: 10453, 1985) and the clotting time was measured. The activity of the recombinant material was shown to be essentially the same as that of naturally occurring protein C.

Protein C produced by transfected BHK and 293 cells was further analyzed by Western blotting. Media samples were electrophoresed on denaturing gels and blots were prepared and probed with radiolabeled antibody to protein C. Results indicated that about 20% of the protein C from BHK cells was in the two-chain form, while about 90% of that from 293 cells was processed to the two-chain form.

TABLE 2

TRANSIENT EXPRESSION AND SECRETION OF PROTEIN C IN COS and 293 CELLS

| cells | plasmid | ng/ml protein C in media |
|---|---|---|
| COS | none | 0 |
| COS | p594 | 10 |
| 293 | none | 0 |
| 293 | p594 | 50 |

EXAMPLE 6

EXPRESSION OF ACTIVATED PROTEIN C

The cDNA sequence for protein C was altered by site-specific mutagenesis to delete the portion encoding the activation peptide. The altered sequence was then transfected into BHK and 293 cells and stably transfected cells were selected. Active protein C was detected in culture media samples from both cell lines.

To delete the activation peptide coding sequence, plasmid p594 was digested with Sst I and the ~880 bp fragment was purified and inserted into the Sst I site of M13mp10. The 12 activation peptide codons were deleted by oligonucleotide-directed deletion mutagenesis (Zoller and Smith, *DNA* 3: 479–488, 1984) using the mutagenic oligonucleotide 5'CTGAAACGACTCATTGAT3'. Replicative form DNA was prepared from mutant phage clones and digested with Sst I. The protein C fragment (~840 bp) was isolated and inserted into Sst I digested p594. The resultant plasmids were screened for proper orientation of the Sst I fragment by restriction mapping using Bgl II. A correct plasmid was selected and designated pPC829. Plasmid pPC829 was sequenced to verify the presence of the desired coding sequence.

Plasmid pPC829 was cotransfected into BHK cells (with plasmid pSVDHFR (Lee et al., *Nature* 294: 228–232, 1981)) and 293 cells (with pKO-neo (Southern and Berg, *J. Mol. Appl. Genet.* 1: 327–341, 1982)) by calcium phosphate coprecipitation (Graham and van der Eb, *Virology* 52: 456–467, 1973). After 48 hours, culture media were harvested and assayed for protein C by ELISA. Results are shown in Table 3. At the same time, cultures were split 1:5 into media containing 500 ug/ml of G418 (293 cells) or 250 nM methotrexate (BHK cells). After 10 days in the presence of selective media, stably transfected colonies were screened for protein C production by immunofilter assay (McCracken and Brown, *BioTechniques*, 82–87, March/April, 1984). Plates were rinsed with PBS or No Serum medium (Dulbecco's plus penicillin-streptomycin, 5 ug/ml vitamin K). Teflon ® mesh was then placed over the cells. Nitrocellulose filters were wetted with PBS or No Serum medium, as appropriate, and placed over the mesh. After four hours' incubation at 37° C., filters were removed and placed in buffer A (50 mM Tris pH 7.4, 5 mM EDTA, 0.05% NP-40, 150 mM NaCl, 0.25% gelatin) for 30 minutes at room temperature. The filters were incubated for 1 hour at room temperature, shaking, in biotin labeled sheep polyclonal antibody to protein C, 1 ug/ml in buffer A. Filters were then washed in buffer A and incubated 1 hour at room temperature, shaking, in avidin-conjugated horseradish peroxidase (Boehringer-Mannheim), 1:1000 in buffer A. Filters were washed in buffer B, then in $H_2O$, and incubated in color reagent (60 mg HRP color development reagent [Bio-Rad], 20 ml methanol, 100 ul $H_2O_2$ in 100 ml 50 mM Tris pH 7.4, 150 mM NaCl). The reaction was stopped by transferring the filters to $H_2O$.

Figure 13:
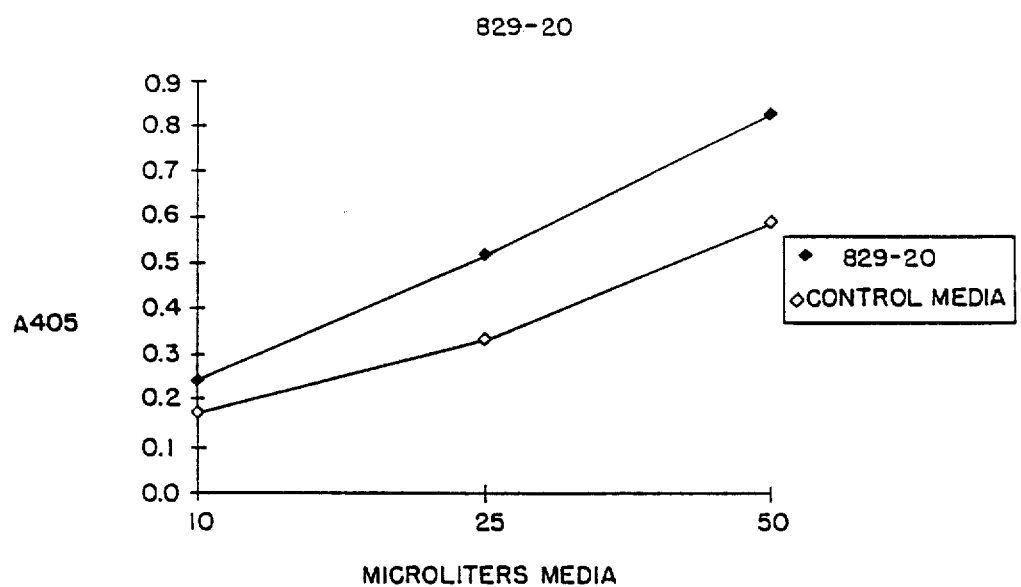
FIG. 13 illustrates the results of an assay for activated protein C on media samples from transfected 293 cells.

Positive colonies were picked and grown in selective media (containing 500 ug/ml G418 or 250 nM methotrexate, as appropriate) for 10 days. Culture media were assayed for APC activity by chromogenic assay. Media samples were added to microtiter wells containing 100 ul of 0.2 mM Spectrozyme PCa (American Diagnostica #336) in 50 mM Tris pH 7.5, 150 mM NaCl. Plates were incubated at 37° C. and the $A_{405}$ measured at various time intervals. Representative results from one transfected 293 cell line (designated 829-20) are shown in FIG. 13. Media from positive colonies of line 829-20 consistently showed higher activity with the chromogenic substrate for APC than did control media which had been incubated with non-transfected 293 cells for the same length of time (10 days).

TABLE 3

TRANSIENT EXPRESSION OF ACTIVATED PROTEIN C (ELISA)

| Cell Line | Protein C ng/ml in Media |
|---|---|
| BHK | 2.7 |

TABLE 3-continued

TRANSIENT EXPRESSION OF ACTIVATED
PROTEIN C (ELISA)

| Cell Line | Protein C ng/ml in Media |
|---|---|
| 293 | 30 |

EXAMPLE 7

USE OF THE FACTOR VII PRE-PRO PEPTIDE TO SECRETE PROTEIN C

The inventors have found that BHK cells correctly process factor VII precursor, but apparently do not remove the leader peptide from protein C at high efficiency. Accordingly, the factor VII pre-pro peptide was substituted for the protein C pre-pro peptide in order to obtain properly processed protein C. This hybrid construct is then inserted into an expression vector and transfected into BHK cells.

A cDNA encoding factor VII has been described (Hagen et al., Proc. Natl. Acad. Sci. USA 83: 2412–2416, Clone λHVII565 comprises the coding sequence for a 38 amino acid pre-pro peptide. This coding sequence was isolated as an Eco RI-Hha I fragment of 140 bp.

The protein C sequence was isolated from p594 by partial cleavage with Sst I and complete digestion with Eco RI. A 1540 bp fragment extending from the Sst I site at codon +7 to the Eco RI site 3' to the cDNA was isolated.

The factor VII and protein C sequences were then joined by means of an oligonucleotide linker which completes the coding sequence for amino acids -3 to -1 of the factor VII pre-pro peptide and amino acids 1-8 of protein C. The linker was constructed from two oligonucleotides having the sequences 5'CCGGCGCGCCAACTCCTTCCTGGAG-GAGCT3' and 5'CCTCCAGGAAG-GAGTTGGCGCGCCGGCG3'. The two oligonucleotides were annealed and joined, in a four-part ligation, to the factor VII pre-pro sequence, protein C cDNA and pUC9 which had been cleaved with Eco RI and treated with bacterial alkaline phosphatase. The ligated DNA was used to transform E. coli (JM 101). Plasmid DNA was prepared and screened for the presence of a 1710 bp Eco RI fragment. A correct clone was designated p7/C-10.

For expression in BHK cells, the Eco RI insert from p7/C-10 is ligated to Eco RI-digested pDX. The resultant vector is used to transfect BHK cells. The cells are cultured and protein C is assayed as previously described.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A DNA sequence which codes for a protein having substantially the same biological activity as human protein C or human activated protein C, said sequence further coding for the pre-pro peptide of factor VII.

2. A DNA sequence which codes for a protein having substantially the same biological activity as human protein C or human activated protein C, said sequence further coding for the amino acid sequence Arg-Arg-Lys-Arg at the cleavage site between the light and heavy chains.

3. An expression vector capable of integration in mammalian host cell DNA, said expression vector including a promoter followed downstream by a nucleotide sequence which encodes a protein having substantially the same biological activity as human protein C or human activated protein C, said nucleotide sequence further encoding the pre-pro peptide of factor VII, said nucleotide sequence being followed downstream by a polyadenylation signal, wherein transcription of the nucleotide sequence is directed by the promoter.

4. An expression vector capable of integration in mammalian host cell DNA, said expression vector including a promoter followed downstream by a nucleotide sequence which encodes the pre-pro peptide of protein C operably linked to a sequence which encodes a protein having substantially the same biological activity as human protein C or human activated protein C, said nucleotide sequence further encoding the amino acid sequence Arg-Arg-Lys-Arg at the cleavage site between the light and heavy chains, said nucleotide sequence being followed downstream by a polyadenylation signal, wherein transcription of the nucleotide sequence is directed by the promoter.

5. Isolated mammalian cells transfected with an expression vector capable of integration in mammalian host cell DNA, said expression vector including a promoter followed downstream by a nucleotide sequence which encodes a protein having substantially the same biological activity as human protein C, said nucleotide sequence further encoding the pre-pro peptide of factor VII, said nucleotide sequence being followed downstream by a polyadenylation signal, wherein transcription of the nucleotide sequence is directed by the promoter.

6. Isolated mammalian cells transfected with an expression vector capable of integration in mammalian host cell DNA, said expression vector including a promoter followed downstream by a nucleotide sequence which encodes the pre-pro peptide of protein C operably liked to a sequence which encodes a protein having substantially the same biological activity as human protein C, said nucleotide sequence further encoding the amino acid sequence Arg-Arg-Lys-Arg at the cleavage site between the light and heavy chains, said nucleotide sequence being followed downstream by a polyadenylation signal, wherein transcription of the nucleotide sequence is directed by the promoter.

7. A method for producing a protein which, upon activation, has substantially the same biological activity as human activated protein C, comprising:

- introducing into an isolated mammalian host cell an expression unit comprising a sequence which encodes a protein having substantially the same biological activity as human protein C, said sequence further coding for the prepro peptide of Factor VII;
- growing said mammalian host cell in an appropriate medium;
- isolating the protein product encoded by said expression unit and produced by said mammalian host cell; and
- activating the protein product to produce a protein having substantially the same biological activity as human activated protein C.

8. The method of claim 7, further comprising introducing into the host cell, with said expression unit, a selectable marker.

9. The method of claim 7 wherein the activating step comprises cleavage of the protein product with a protease selected from the group consisting of α-thrombin, trypsin, and Russell's viper venom factor X activator.

10. The method of claim 7 wherein said nucleotide sequence further encodes the amino acid sequence Arg-Arg-Lys-Arg at the cleavage site between the light and heavy chains.

11. The method of claim 7 wherein said mammalian host cell is selected from the group consisting of COS, BHK and 293 cells.

12. A method for producing a protein which has substantially the same biological activity as human activated protein C, comprising:
 introducing into an isolated mammalian host cell an expression unit comprising a sequence which encodes the pre-pro peptide of protein C operably linked to a sequence which encodes a protein having substantially the same biological activity as human activated protein C, said sequence further encoding the amino acid sequence Arg-Arg-Lys-Arg at the cleavage site between the light and heavy chains;
 growing said mammalian host cell in an appropriate medium; and
 isolating the protein product encoded by said expression unit and produced by said mammalian host cells.

13. The method of claim 12 wherein said mammalian host cell is selected from the group consisting of COS, BHK and 293 cells.

14. A method for producing a protein which, upon activation, has substantially the same biological activity as human activated protein C, comprising:
 introducing into an isolated mammalian host cell an expression unit comprising a sequence which encodes the pre-pro peptide of protein C operably linked to a sequence which encodes a protein having substantially the same biological activity as human protein C, said sequence further coding for the amino acid sequence Arg-Arg-Lys-Arg at the cleavage site between the light and heavy chains;
 growing said mammalian host cell in an appropriate medium;
 isolating the protein product encoded by said expression unit and produced by said mammalian host cell; and
 activating the protein product to produce a protein having substantially the same biological activity as human activated protein C.

15. The method of claim 14 wherein the activating step comprises cleavage of the protein product with a protease selected from the group consisting of α-thrombin, trypsin, and Russell's viper venom factor X activator.

16. The method of claim 14 wherein said mammalian host cell is selected from the group consisting of COS, BHK and 293 cells.

17. The DNA sequence of claims 1 or 2, wherein said protein comprises the light chain of protein C as shown in FIG. 2 from alanine, amino acid number 1, to leucine, amino acid number 155, and the heavy chain of human activated protein C as shown in FIG. 2 from leucine, amino acid number 170, to proline, amino acid number 419.

18. The expression vector of claims 3 or 4, wherein said protein comprises the light chain of protein C as shown in FIG. 2 from alanine, amino acid number 1, to leucine, amino acid number 155, and the heavy chain of human activated protein C as shown in FIG. 2 from leucine, amino acid number 170, to proline, amino acid number 419.

19. The cells of claims 5 or 6, wherein said protein comprises the light chain of protein C as shown in FIG. 2 from alanine, amino acid number 1, to leucine, amino acid number 155, and the heavy chain of human activated protein C as shown in FIG. 2 from leucine, amino acid number 170, to proline, amino acid number 419.

20. The method of any one of claims 7, 12, or 14, wherein said protein comprises the light chain of protein C as shown in FIG. 2 from alanine, amino acid number 1, to leucine, amino acid number 155, and the heavy chain of human activated protein C as shown in FIG. 2 from leucine, amino acid number 170, to proline, amino acid number 419.

* * * * *

UNITED STATES PATENT AND TRADEMARK OFFICE
CERTIFICATE OF CORRECTION

PATENT NO. : 4,959,318
DATED : September 25, 1990
INVENTOR(S) : Donald C. Foster et al.

It is certified that error appears in the above-identified patent and that said Letters Patent is hereby corrected as shown below:

In claim 7, column 22, line 59, please delete "prepro" and substitute therefor, --pre-pro--.

Signed and Sealed this

Eleventh Day of February, 1992

Attest:

HARRY F. MANBECK, JR.

*Attesting Officer*     *Commissioner of Patents and Trademarks*